US008317823B2

(12) United States Patent
Pavcnik et al.

(10) Patent No.: US 8,317,823 B2
(45) Date of Patent: Nov. 27, 2012

(54) BODILY LUMEN CLOSURE APPARATUS AND METHOD

(75) Inventors: Dusan Pavcnik, Portland, OR (US); John Kaufman, Lake Oswego, OR (US); Clay D. Fette, Lebanon, IN (US)

(73) Assignees: Cook Biotech Incorporated, West Lafayette, IN (US); Oregon Health Science University, Portland, OR (US)

( * ) Notice: Subject to any disclaimer, the term of this patent is extended or adjusted under 35 U.S.C. 154(b) by 0 days.

(21) Appl. No.: 12/109,574

(22) Filed: Apr. 25, 2008

(65) Prior Publication Data
US 2008/0215087 A1 Sep. 4, 2008

Related U.S. Application Data

(63) Continuation of application No. 10/843,990, filed on May 12, 2004, which is a continuation-in-part of application No. 10/206,480, filed on Jul. 26, 2002.

(60) Provisional application No. 60/470,611, filed on May 15, 2003, provisional application No. 60/307,893, filed on Jul. 26, 2001.

(51) Int. Cl.
*A61B 17/08* (2006.01)
(52) U.S. Cl. ..................... 606/213; 623/23.72
(58) Field of Classification Search .......... 128/830, 128/831, 887; 623/23.72; 606/190, 193, 606/194, 197, 213; 600/29, 32
See application file for complete search history.

(56) References Cited

U.S. PATENT DOCUMENTS

| 3,858,571 A | 1/1975 | Rudolph |
| 4,292,972 A | 10/1981 | Pawelchak et al. |
| 4,347,234 A | 8/1982 | Wahlig et al. |
| 4,404,970 A | 9/1983 | Sawyer |
| 4,412,947 A | 11/1983 | Cioca |
| 4,512,342 A | 4/1985 | Zaneveld et al. |

(Continued)

FOREIGN PATENT DOCUMENTS
EP 1182973 12/2004
(Continued)

OTHER PUBLICATIONS

"Part 17: Gastrointestinal Tract", part of the Lumen Histology Slide Series, http://www.meddean.luc.edu/lumen/MEdEd/Histo/frames/h_fram17.html.

(Continued)

*Primary Examiner* — Patricia Bianco
*Assistant Examiner* — Camtu Nguyen
(74) *Attorney, Agent, or Firm* — Woodard, Emhardt, Moriarty, McNett & Henry LLP

(57) ABSTRACT

An absorbable and expandable closure member used to occlude or exclude a body lumen or cavity, such as a blood vessel, fallopian tube, duct, aneurysmal sac, etc., comprising a closure member comprising one of more sheets of a biomaterial that are rolled, stacked, or folded to form a multilayer construct of a generally cylindrical configuration for deployment through a delivery system, either as a singularly or part of a multiplicity of closure members. The biomaterial is derived from a source material, such as small intestinal submucosa or another remodelable material (e.g., an extracellular matrix) having properties for stimulating ingrowth of adjacent tissue into the biomaterial deployed within the bodily lumen. The closure member is deployed to the bodily lumen from a delivery sheath, cartridge, and/or over a inner guiding member, such as a wire guide or catheter.

17 Claims, 14 Drawing Sheets

U.S. PATENT DOCUMENTS

| | | | |
|---|---|---|---|
| 4,606,337 A | | 8/1986 | Zimmermann et al. |
| 4,616,998 A | * | 10/1986 | Wong .......................... 433/73 |
| 4,705,517 A | | 11/1987 | DiPisa, Jr. |
| 4,852,568 A | | 8/1989 | Kensey |
| 4,890,612 A | | 1/1990 | Kensey |
| 4,948,540 A | | 8/1990 | Nigam |
| 4,981,465 A | | 1/1991 | Ballan et al. |
| 5,021,059 A | | 6/1991 | Kensey et al. |
| 5,061,274 A | | 10/1991 | Kensey |
| 5,192,302 A | | 3/1993 | Kensey et al. |
| 5,222,974 A | | 6/1993 | Kensey et al. |
| 5,224,493 A | | 7/1993 | Sawan et al. |
| 5,282,827 A | | 2/1994 | Kensey et al. |
| 5,310,407 A | * | 5/1994 | Casale ......................... 604/506 |
| 5,334,216 A | | 8/1994 | Vidal et al. |
| 5,374,261 A | | 12/1994 | Yoon |
| 5,382,261 A | | 1/1995 | Palmaz |
| 5,383,886 A | | 1/1995 | Kensey et al. |
| RE34,866 E | | 2/1995 | Kensey et al. |
| 5,391,183 A | | 2/1995 | Janzen et al. |
| 5,437,631 A | | 8/1995 | Janzen |
| 5,441,517 A | | 8/1995 | Kensey et al. |
| 5,456,693 A | | 10/1995 | Conston et al. |
| 5,514,158 A | * | 5/1996 | Kanesaka ..................... 606/213 |
| 5,522,840 A | | 6/1996 | Krajicek |
| 5,531,759 A | | 7/1996 | Kensey et al. |
| 5,545,178 A | | 8/1996 | Kensey et al. |
| 5,571,181 A | | 11/1996 | Li |
| 5,584,827 A | | 12/1996 | Korteweg et al. |
| 5,591,204 A | | 1/1997 | Janzen et al. |
| 5,643,317 A | | 7/1997 | Pavcnik et al. |
| 5,656,036 A | | 8/1997 | Palmaz |
| 5,665,114 A | * | 9/1997 | Weadock et al. ............. 623/1.34 |
| 5,676,689 A | | 10/1997 | Kensey et al. |
| 5,681,334 A | * | 10/1997 | Evans et al. .................. 606/148 |
| 5,707,393 A | | 1/1998 | Kensey et al. |
| 5,709,934 A | | 1/1998 | Bell et al. |
| 5,716,375 A | * | 2/1998 | Fowler ......................... 606/213 |
| 5,725,498 A | | 3/1998 | Janzen et al. |
| 5,741,223 A | | 4/1998 | Janzen et al. |
| 5,752,974 A | | 5/1998 | Rhee et al. |
| 5,830,130 A | | 11/1998 | Janzen et al. |
| 5,861,004 A | | 1/1999 | Kensey et al. |
| 5,916,265 A | | 6/1999 | Hu |
| 5,935,147 A | | 8/1999 | Kensey et al. |
| 5,947,997 A | | 9/1999 | Pavcnik et al. |
| 5,948,425 A | | 9/1999 | Janzen et al. |
| 5,955,110 A | | 9/1999 | Patel et al. |
| 6,090,996 A | * | 7/2000 | Li ................................ 623/23.64 |
| 6,096,080 A | | 8/2000 | Nicholson et al. |
| 6,190,353 B1 | | 2/2001 | Makower et al. |
| 6,245,527 B1 | | 6/2001 | Busfield et al. |
| 6,312,474 B1 | | 11/2001 | Francis et al. |
| 6,358,284 B1 | | 3/2002 | Fearnot et al. |
| 6,432,116 B1 | | 8/2002 | Callister et al. |
| 6,482,179 B1 | * | 11/2002 | Chu et al. .................. 604/164.09 |
| 6,540,735 B1 | * | 4/2003 | Ashby et al. .................. 604/523 |
| 6,569,081 B1 | | 5/2003 | Nielsen et al. |
| 7,153,324 B2 | | 12/2006 | Case et al. |
| 7,166,133 B2 | | 1/2007 | Evans et al. |
| 7,175,652 B2 | | 2/2007 | Cook et al. |
| 2001/0041900 A1 | | 11/2001 | Callister et al. |
| 2004/0087998 A1 | | 5/2004 | Lee et al. |
| 2005/0013844 A1 | | 1/2005 | Hadlock et al. |
| 2005/0049626 A1 | | 3/2005 | Burgard |
| 2008/0027477 A1 | | 1/2008 | Obermiller |

FOREIGN PATENT DOCUMENTS

| | | |
|---|---|---|
| FR | 2522959 | 9/1983 |
| RU | 2180529 | 3/2002 |
| SU | 1673130 | 8/1991 |
| SU | 1690737 | 11/1991 |
| SU | 1718837 | 3/1992 |
| WO | WO 87/00062 | 1/1987 |
| WO | WO 92/06639 | 2/1993 |
| WO | WO 94/26175 | 11/1994 |
| WO | WO 97/19643 | 6/1997 |
| WO | WO 98/22158 | 5/1998 |
| WO | WO 98/25545 | 6/1998 |
| WO | WO 00/13624 | 3/2000 |
| WO | WO 00/32112 | 6/2000 |
| WO | WO 00/32250 | 6/2000 |
| WO | WO 00/32253 | 6/2000 |
| WO | WO 00/72759 | 12/2000 |
| WO | WO 00/74576 | 12/2000 |
| WO | WO 01/45765 A1 * | 6/2001 |
| WO | WO 2005/020823 | 3/2005 |
| WO | WO 2005/030035 | 4/2005 |
| WO | WO 2005/070302 | 8/2005 |
| WO | WO 2006/119256 | 11/2006 |
| WO | WO 2007/002260 | 1/2007 |
| WO | WO 2007/011443 | 1/2007 |
| WO | WO 2007/064819 | 6/2007 |
| WO | WO 2007/090150 | 8/2007 |
| WO | WO 2007/090155 | 8/2007 |

OTHER PUBLICATIONS

Arterial Puncture Site Management; Stephen T. Kee, MD; Applied Radiology, pp. 7-12, Jul. 2000.

Chapter 10, "The Peridardium", Handbook of Pathology and Pathophysiology of Cardiovascular Disease, vol. 240, Springer Netherlands (2002).

Pamphlet on Peripheral Vascular Disease; Datascope Collagen Products; VasoSeal; four pages, unknown date.

Endoluminal Stenting; Chapter 45, Kenneth R. Kensey; Chapter 46, Artur M Spokojny and Timothy A. Sanborn; and Chapter 48, Nicholas N. Kipshidze, Joseph B. Horn, Victor Nikolaychik and John E. Baker, edited by Ulrich Sigwart; W.B. Saunders 1996.

Heeschen, C., et al. "Nicotine Stimulates Angiogenesis and Promotes Tumor Growth and Atherosclerosis", Nature Medicine, vol. 7., No. 7, Jul. 2001, pp. 833-839.

Himpson, Rebecca C., et al. "Histological evidence for enhanced anal fistula repair using autologous fibroblasts in a dermal collagen matrix." Comparative Clinical Pathology, Apr. 2006, vol. 16, No. 1.

Information from Vascular Solutions web site (www.vascularsolutions.com) on Duett sealing device; two pages, 2001.

Information from Vasoseal web site (www.vasoseal.com) on VasoSeal ES, three pages, 2001.

Information from Vasoseal web site (www.vasoseal.com) on VascSeal VHD, three pages, 2001.

Information from web site (www.pbm.ct.utwente.nl/dopdrachten/wonder.htm) on Nerve Regeneration, three pages, 2001.

Johnson, C. et al. "Matrix Metalloproteinase-9 is Required for Adequate Angiogenic Revascularization of Ischemic Tissues: Potential Role in Capillary Branching", Circulation Research, vol. 94 (2004) pp. 262-268.

Khairy, G.E.A. et al., "Percutaneous obliteration of duodenal fistula", J.R. Coll. Surg. Edinb., 45, Oct. 2000, 342-344.

Lisle, David A., et al., "Percutaneous Gelfoam Embolization of Chronic Enterocutaneous Fistulas: Report of Three Cases", Diseases of the Colon & Rectum, vol. 50, No. 2, Dec. 2006.

Maluf-Filho, F. et al., "Endoscopic Treatment of Esophagogastric Fistulae with an Acellular Matrix", Gastrointestinal Endoscopy, Elsevier, NL, vol. 59, No. 5, Apr. 2004, p. 151, XP004854594 abstract.

Miklos, J.R., et al., "Rectovaginal Fistula Repair Utilizing a Cadaveric Dermal Allograft", International Urogynecology Journal, 1999, vol. 10, No. 6, pp. 405-406.

Moore, Robert D., et al., "Rectovaginal Fistula Repair Using a Porcine Dermal Graft", Obstetrics & Gynecology, 2004, 104, 1165-1167.

Schultz, David J., et al., "Porcine Small Intestine Submucosa as a Treatment for Enterocutaneous Fistulas", Journal of American College of Surgeons, 2002, vol. 194, No. 4, Apr. 2002, pp. 541-543.

Schwesinger, Wyne H., "Management of Persistent Fistula After Gastrectomy" online question (www.medscape.com), posted on May 14, 2002.

Shah, A.M. et al., "Bronchoscopic closure of bronchopleural fistula using gelfoam", abstract. Journal of Association of Physicians of India, 2004, vol. 52 No. JUIN, pp. 508-509.

Shaker MA, Hindy AM, Mounir RM, Geaisa KM. Egypt Dent. J. Jul. 1995; 41(3): 1237-42.

Sheiman, Robert G., et al., "Percutaneous Treatment of a Pancreatic Fistula after Pancreaticoduodenectomy", J Vasc Interv Radiol, 2001, vol. 12, No. 4, pp. 524-526.

Shelton, Andrew A., et al., Transperineal Repair of Persistent Rectovaginal Fistulas Using an Accelular Cadaveric Dermal Grant (AlloDerm). Diseases of the Colon & Rectum, Sep. 2006, Vo.. 49, No. 9.

Usefulness of Collagen Plugging with VasoSeal after PTCA as Compared to Manual Compressionwith Identical Sheath Dwell Times; Sigmund Silber, MD, Aina Bjorvik, Holer Muhling, MD, Andreas Rosch, MD, Cathet. Cardiovasc. Diagn. 43:421-427, 1998.

Wilson Gunn on behalf of unnamed party, Letter to the European Patent Office, Jan. 30, 2007, pp. 1-4.

* cited by examiner

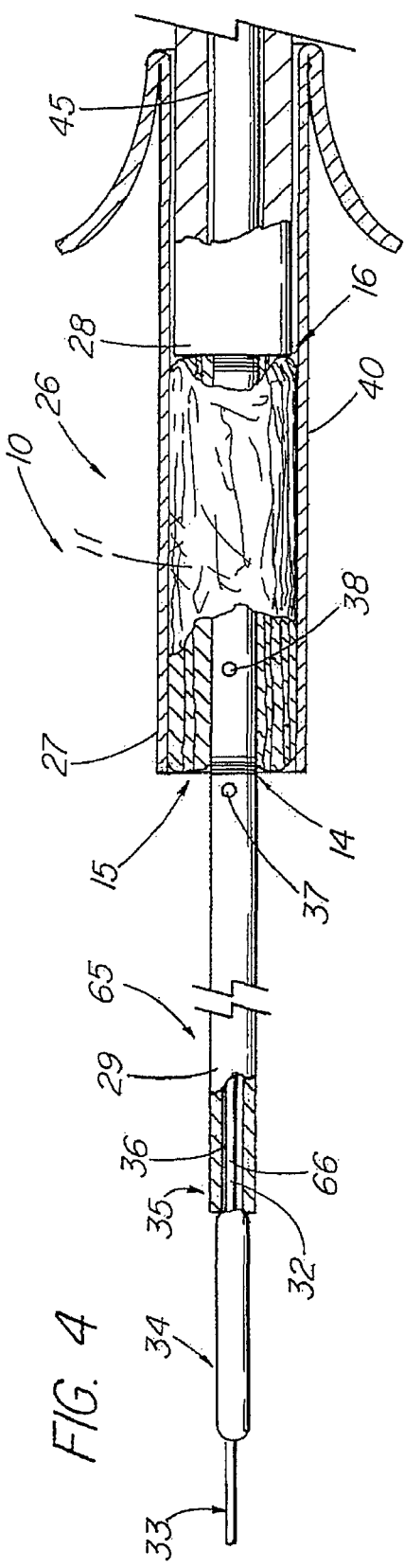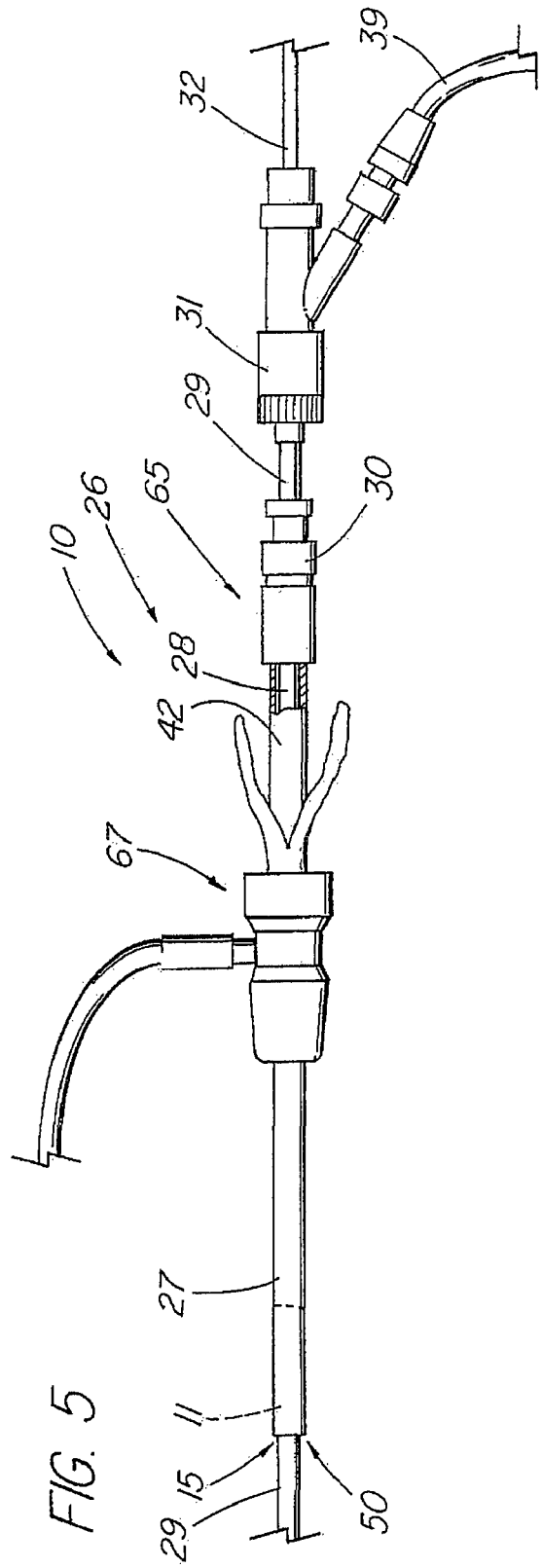
FIG. 4
FIG. 5

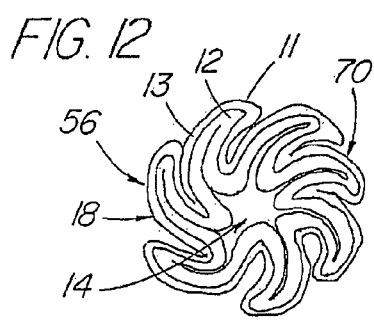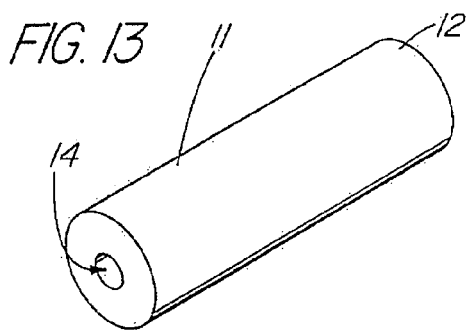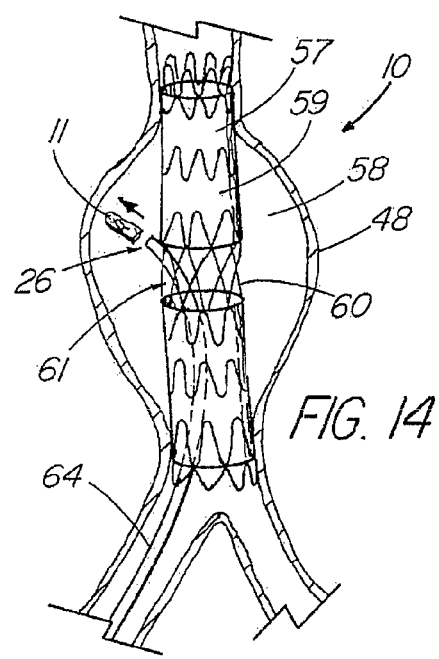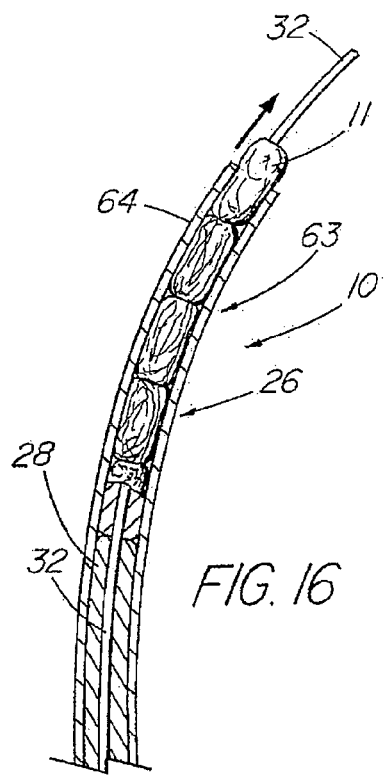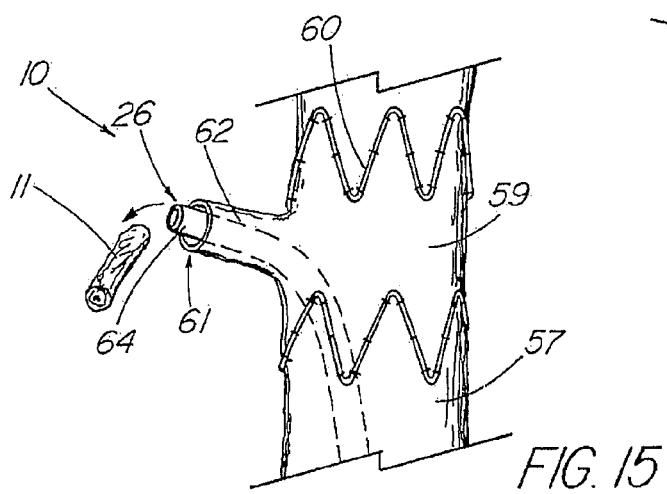

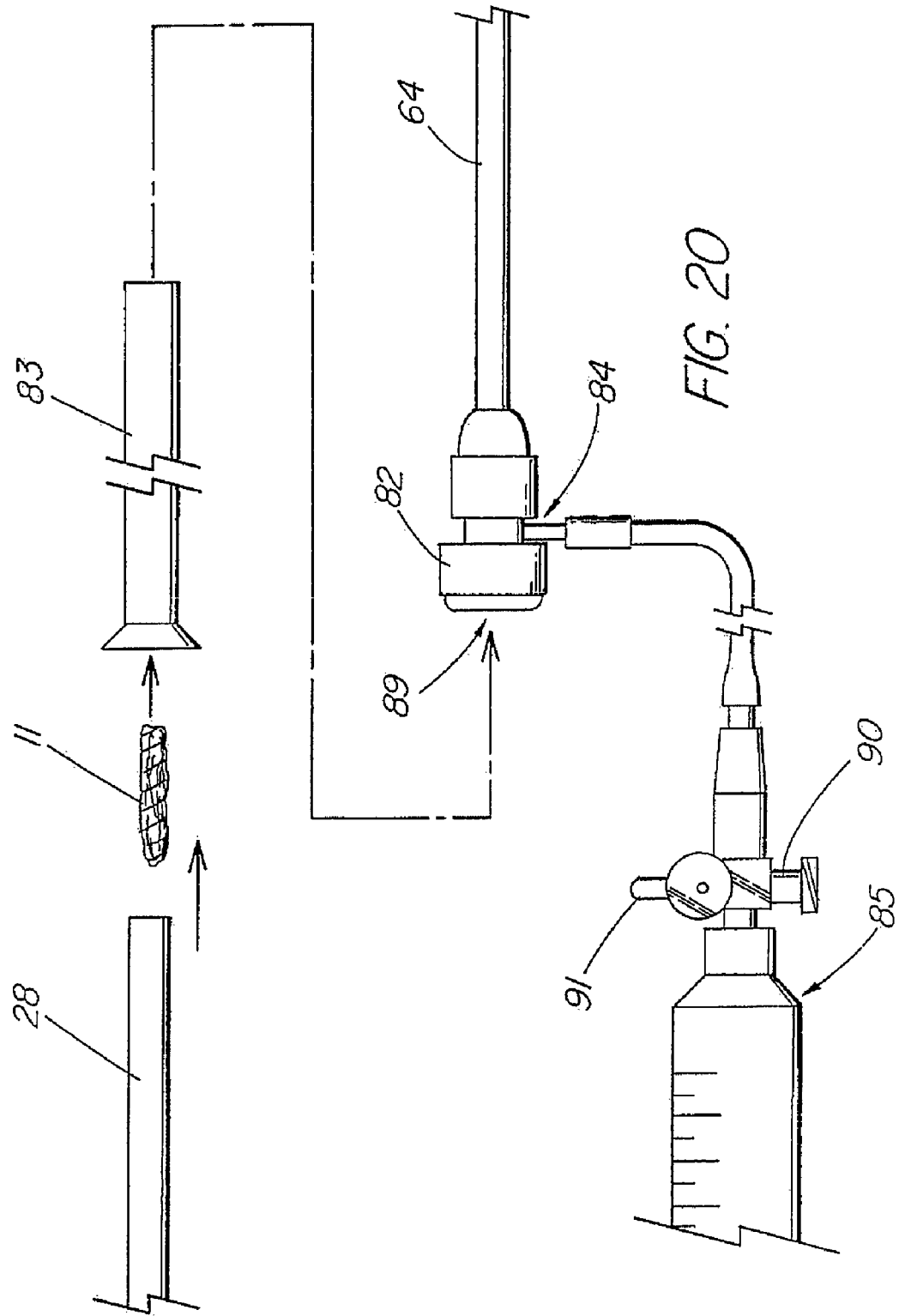

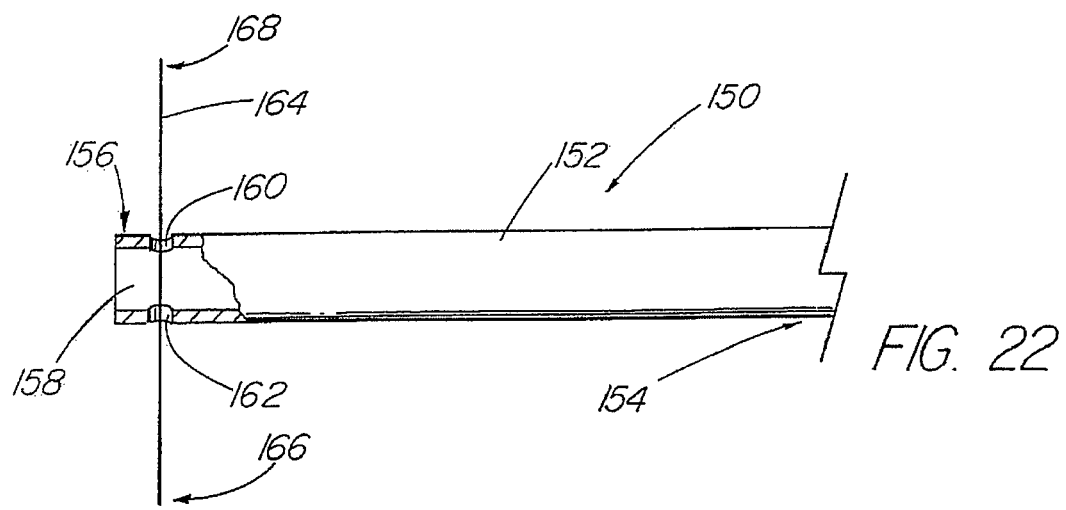
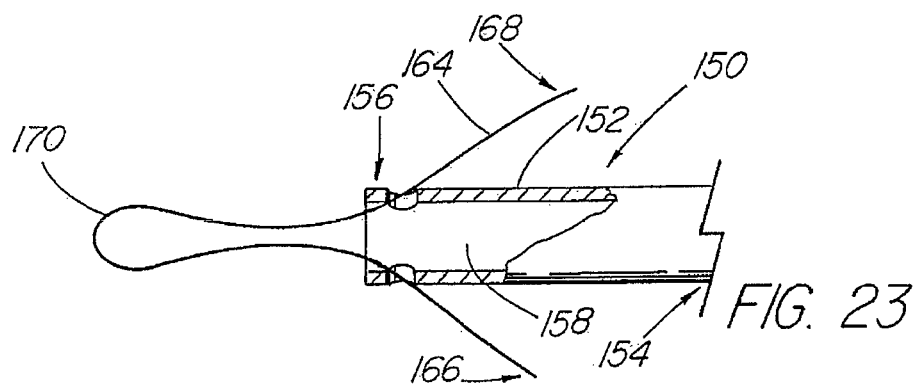
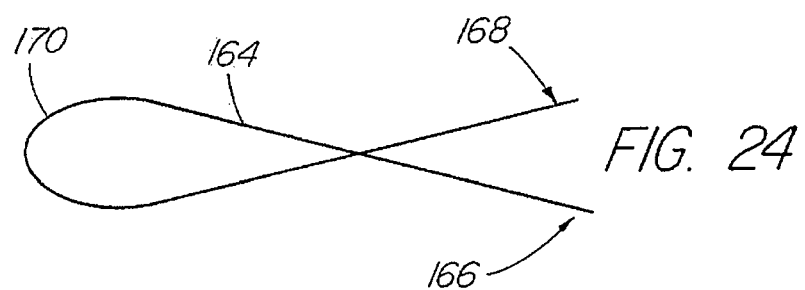

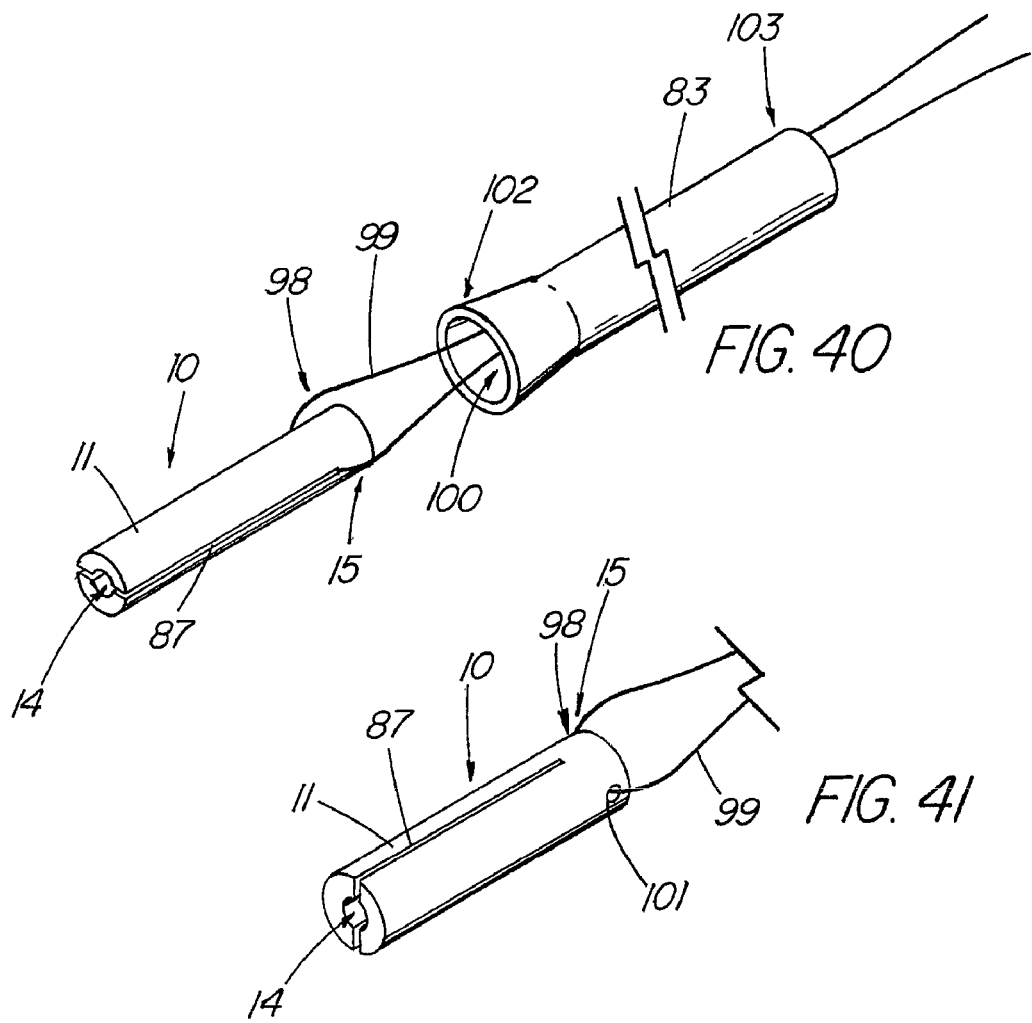
FIG. 40
FIG. 41
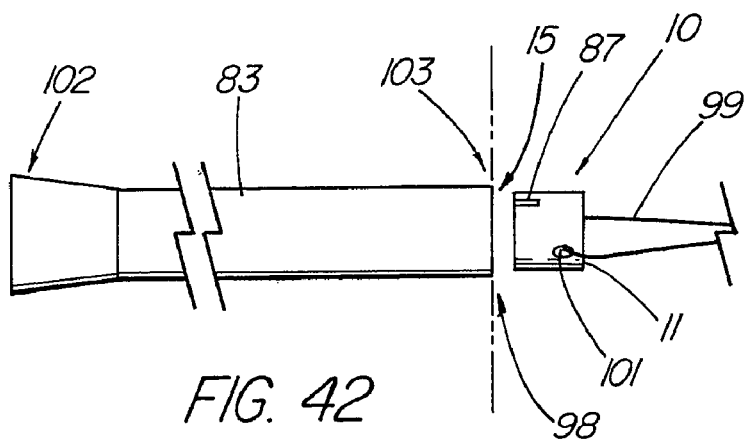
FIG. 42

BODILY LUMEN CLOSURE APPARATUS AND METHOD

CROSS-REFERENCE TO RELATED APPLICATIONS

This application claims the benefit of U.S. Provisional Application Ser. No. 60/470,611 filed May 15, 2003, and is a continuation of U.S. patent application Ser. No. 10/843,990 filed May 12, 2004, which is a Continuation-in-Part of U.S. application Ser. No. 10/206,480 filed Jul. 26, 2002, which claims the benefit of U.S. Provisional Patent Application Ser. No. 60/307,893 filed Jul. 26, 2001.

TECHNICAL FIELD

This invention relates to medical devices, more particularly to vessel closure members, delivery apparatuses, and methods of inserting the closure members.

BACKGROUND OF THE INVENTION

Open surgical procedures which require incisions through skin, tissue, and organs have a traumatic effect on the body and can lead to substantial blood loss. In addition, such procedures expose tissue and organs to the outside environment which creates an increased risk of post-operative infection. After open surgical procedures, patients are generally in pain, require substantial recovery time, and are susceptible to post-operative complications. As a result, open surgical procedures are generally higher in cost and have a higher degree of risk.

Because of the problems associated with open surgical procedures, the use of minimally invasive surgical techniques has grown substantially over the recent years. As these techniques have developed, the number and types of treatment devices, including vessel closure members, have proliferated. Vessel closure members are generally used for sealing fluid passageways in patients, including but not limited to, percutaneous sites in femoral arteries or veins resulting from intravascular procedures, cardiovascular deformations, fallopian tubes and the vas deferens to prevent conception, and vessels in the brain. Recently, much focus has been placed on developing closure members which allow quicker hemostasis during intravascular procedures and closure members which quickly and effectively occlude fallopian tubes or the vas deferens to prevent conception.

Intravascular Closure Members

One of the important benefits of minimally invasive intravascular procedures is less patient blood loss; however, particularly in procedures in which the femoral artery is accessed, achieving quick and effective hemostasis at the puncture site still can be problematic. More recently, the increased use of heparin and larger sized introducer sheaths have presented additional challenges. When larger devices are introduced into an artery or vein, e.g., 5 Fr or larger, external manual or mechanical compression applied at the entry site, commonly the femoral artery or vein, has been the standard method of achieving hemostasis, which occurs when a thrombus forms at the vessel opening, thereby preventing further bleeding at the site. External compression typically requires that the constant, firm pressure is maintained for up to 30 minutes until hemostasis has been achieved. Even after hemostasis, the site remains vulnerable to further bleeding, especially if the patient is moved.

To address the obvious inadequacies of using manual or external compression alone to close a percutaneous site, a number of devices have been developed to assist in closure of the entry site. Various suturing devices have been developed by Perclose, Inc. and sold by Abbott Laboratories (Redwood City, Calif.) which deliver needles that penetrate the arterial wall to form a knot to close the puncture site. While suturing produces relatively quick and reliable hemostasis when compared to external compression, it is a technique that requires much skill and experience on the part of the physician. In addition, the complexity of the device has led to reports of failures such as in the ability to form a proper knot and other problems. Another known complication is when the device is deployed such that the needles penetrate completely through the opposite wall of the target vessel, which can inadvertently lead to the vessel being closed off, a potentially serious event for the patient. Hemostatic collagen plugs offer a lower cost, simpler alternative to suturing devices and they have increased in popularity, particularly the VASOSEAL® (Datascope Corp., Montvale, N.J.) and ANGIOSEAL™ (The, Kendall Co., Mansfield Mass.) closure devices. VASOSEAL® comprises a bovine collagen sponge plug that is pushed through a blunt tract dilator through the tissue puncture channel where it is deployed against the outer vessel wall to seal the puncture site. The collagen plug swells with blood and helps occlude blood flow. Manual pressure is still required following initial hemostasis until thrombosis formation is sufficient. Complications can occur from the dilator entering the vessel where the collagen can be accidentally deployed. Placement of the device also requires that the depth of the tissue channel be pre-measured to achieve satisfactory placement. The ANGIOSEAL™ device is similar except that it includes a prosthetic anchorplate that is left inside the vessel where it biodegrades in about 30 days. Re-puncture at the site can typically occur at that time at the site, but may be problematic if the anchor device has not been reabsorbed. Additionally both closure devices, being made of bovine collagen, can cause the formation of fibrotic tissue in some patients, which in severe cases, has been known to be sufficient to restrict blood flow within the vessel. A third device utilizing collagen is the DUETT™ sealing device (Vascular Solutions Inc., Minneapolis, Minn.), which comprises a balloon catheter that delivers a collagen and thrombin solution to the puncture site, which causes fibrinogen formation that seals the puncture site. Generally, collagen plugs have been of limited use in closing larger punctures sites and are typically intended for procedures involving 5-8 Fr introducer sheaths. Even suturing devices are intended for closing puncture sites in the small to moderate range, although some physicians have reportedly been able to perform an additional series of steps to suture larger arterial puncture sites, adding to the time and complexity of the procedure.

Fallopian Tube Closure Members

Currently available methods for permanently occluding or closing fallopian tubes and the vas deferens to prevent conception include tubal ligations and vasectomies. Both of these procedures, however, are invasive, are not generally performed in the doctor's office, and can be expensive. Prior art methods of occluding the fallopian tubes include placing an elastomeric plug or other member in the isthumus or narrow most portion of the fallopian tubes. These elastomeric plugs or other members, however, often migrate in the fallopian tube or otherwise become dislodged allowing sperm to pass through the fallopian tube and fertilize an egg released by an ovary. Another prior art fallopian tube occlusion device is disclosed in Nikolchev et al., U.S. Pat. No. 6,176,240 B1. Nikolchev et al. discloses a metallic coil which is pre-shaped into multiple loops separated by straight sections or pre-shaped into a "flower coil." The metallic coil is inserted into the fallopian tube in an elongated state and when deployed returns to the "flower coil" shape which has a larger diameter than the fallopian tube. The fallopian tube occlusion device of Nikolchev et al. is complicated requiring the metallic coil to be pre-formed into a flower shape which must have a diameter larger than the interior of the fallopian tube, or the device will not lodge in the fallopian tube.

What is needed is a simple to use, relatively inexpensive, closure member that can provide safe and efficient closure of both smaller and larger vessels, including femoral veins and arteries, fallopian tubes, and the vas deferens. Ideally, such a member should be compatible with other instrumentation used in the procedure, it should be highly biocompatible, and it should allow subsequent access at the entry site after a reasonable period of time without further complications. In addition, the closure member should be designed for use with a delivery system that allows precise placement without having to pre-measure the tissue channel leading to the vessel, permits the closure member to be reliably placed in the desired location, and delivers the closure member easily and reliably in the vessel or against the vessel wall.

SUMMARY OF THE INVENTION

The foregoing problems are solved and a technical advance is achieved in an illustrative closure apparatus and delivery system for delivering a closure member (or 'construct'), typically an absorbable member comprising an extracellular matrix material or other bioremodelable material, within a body lumen or cavity to substantially restrict or occlude passage of fluids or other bodily materials therethrough or thereinto. In a first embodiment of the invention, the closure apparatus comprises a construct adapted to function as a hemostatic member. The hemostatic member typically comprises a generally cylindrical shape construct that is highly expandable In volume when exposed to blood. In one embodiment, the hemostatic member includes a functional passageway that allows the closure member to be mounted over a medical device, such as a delivery catheter or wire guide, for delivery against a vessel puncture or into another vascular environment, such as to fill an aneurysm sac, to treat an AV, gastroenteric, or extravascular fistula, treat an arterial or venous malformation, or to occlude a vessel. As used herein, functional passageway is defined as any longitudinal pathway extending through, or substantially through the hemostatic member and through which a medical device, such as a catheter or wire, can pass, and which offers little or minimal resistance such that the structure of the material(s) of construction are not broken, torn, or otherwise disrupted. An example of a non-function pathway would be where a device is forced through a foam or sponge material where a passageway is not already substantially preformed such that the cells of the foam must be mechanically separated as the device is forced therethrough. Besides open lumens, examples of functional pathways would include self-sealing membranes or valves, gel-like or sealant materials, and compressed, rolled or folded constructs which have natural spaces between layers through which a medical device could pass.

In a second aspect of the invention, the hemostatic member includes a first material, such as a foam material, which is capable of absorbing blood to expand several times (e.g., 6-10x) its diameter to cause hemostasis, and a second material, such as a sheet of a biomaterial which provides structural integrity (biomaterial being defined herein as any biologically derived material or synthetic matrix material that includes growth factors or other biologically active compounds). In one embodiment used to close arterial or venous punctures made during common intravascular procedures, the hemostatic member comprises a sheet of an extracellular collagen matrix (ECM), such as small intestinal submucosa (SIS), which is rolled together with a SIS sponge comprising lyophilized and comminuted SIS that has been formed into a thin layer and cross-linked using one of several known cross-linking agents. It is the highly-absorbent sponge material that provides most of the radial expansion of the hemostatic member. The sheet of SIS, when rolled into a generally cylindrical construct along with the adjacent sheet of sponge material, adds structural integrity to the construct, allowing it to be used to seal larger puncture channels, such as 9-16 Fr, which typically fall outside the capabilities of collagen foam plugs. This is due primarily to the fact that the harvested SIS sheet material generally maintains its structure much longer than the ground collagen or SIS sponge when wet. Collagen sponge plugs essentially liquefy when exposed to blood and although then are able to shorten the time of hemostasis in punctures involving introducers up to 8 Fr in diameter, they are not indicated for sealing larger puncture sites. The two rolled sheets of SIS are compressed into a cylindrical construct and placed over a delivery catheter. Ideally, the hemostatic member comprises no more than half the length of tissue tract, which typically measures 3-4 cm in an average patient. It is within the scope of the invention for hemostatic member to comprise only the second material, such as a tightly rolled SIS construct, or it could include only the first, foam or sponge-like material (e.g., lyophilized SIS). For example, treating lyophilized SIS with more effective cross-linking agents could yield a construct having increased structural integrity that is comparable to the illustrative hemostatic member that includes a SIS sheet. SIS and other ECM biomaterials provide a clinical advantage over biomaterials containing mammalian cells or cellular debris in that they can be processed to be both highly biocompatible and thus, much better tolerated than traditional collagen-based implants. SIS is known to have the ability to stimulate angiogenesis and tissue ingrowth to become completely remodeled as host tissue over time. The process of obtaining purified SIS is described in U.S. Pat. No. 6,209,931 to Cook et. al.

The hemostatic member delivery apparatus includes an outer sheath member, such as an introducer sheath, which may represent the same sheath that is initially used in the intravascular procedure, a pusher member to provide counter force to hold the hemostatic member in place while the sheath is being withdrawn, and a wire guide which extends through the lumen of the mounting catheter and provides an atraumatic distal tip within the vessel. One method of delivering the hemostatic member to externally seal a puncture site includes the steps of loading the hemostatic member subassembly (which also includes the mounting catheter, wire guide, and pusher member) into the introducer sheath while the sheath is within the vessel. A splittable cartridge can be used to temporarily constrain the hemostatic member to facilitate the loading process into the introducer sheath. The hemostatic member subassembly is configured to correspond to the length of the introducer sheath such that when it is fully advanced into the sheath, the hemostatic member is positioned near the distal end of the introducer member. The introducer sheath and hemostatic member subassembly are partially withdrawn from the vessel such that the blunt end of the introducer sheath is outside the vessel. The opening narrows as the elastic vessel walls retract after the introducer sheath is withdrawn such that re-advancement would cause the introducer sheath to abut the outside of the vessel or tunica vascularis about the puncture site. An optional side hole is located on the delivery catheter just distal to the distal end to the hemostatic member which can provide a positional indicator for the delivery subassembly. Blood flowing into the side hole and through the delivery catheter, can be observed by the operator as it flows into a side port catheter, indicating that the tip of the introducer sheath is still outside the vessel. To make it such that blood can only enter the lumen of the mounting catheter though the side hole, a section of the distal portion of the wire guide can be made larger to act as a seal against the distal end of the mounting catheter.

With the distal tip of the introducer sheath abutting the vessel, the hemostatic member is deployed. A splittable deployment guard placed between the hub of the introducer sheath and the pusher member can be used to prevent accidental premature deployment. Once it is removed, the introducer sheath can be partially withdrawn, while holding the pusher member in position, to expose either a part or all of the hemostatic member to blood and allow it to expand within the tissue tract. An optional second side hole may be formed within the region over which the hemostatic member is mounted. The wire guide can either be advanced to allow blood to flow into the lumen of the mounting catheter, or it can be withdrawn from the mounting catheter lumen to allow blood to flow through the second side hole. Deployment of the hemostatic member against the vessel is accomplished by partial withdrawal of the introducer sheath, while the pusher member is maintained in position for a few minutes until the hemostatic member has swelled to its fully expanded state and has stabilized. The delivery catheter is removed from the pathway of the hemostatic member which swells to quickly seal any lumen left by its withdrawal. The pusher member is removed with the introducer member after stabilization, and external or mechanical compression is applied at the site for the recommended period of time or until the physician feels it is no longer necessary.

In another aspect of the invention, the distal end of the hemostatic member includes a plurality of slits, such as two slits dividing the hemostatic member lengthwise into quarters and which extend for about 25-30% of its length. Slitting the distal portion of hemostatic member allows the distal end to expand outward to facilitate the sealing process.

In still other aspects of the invention, the second (sheet) material of the hemostatic member includes a folded, rather than a rolled configuration, which unfolds as the hemostatic member radially expands within the tissue channel. The folds can include any number of configurations such as radially-arranged pleat or parallel folds with the foam sheet typically being interspersed between the folds.

In yet another aspect of the invention, the hemostatic member delivery apparatus can be adapted to introduce the hemostatic member into an aneurysm to prevent leakage around a stent graft. In one embodiment, the stent graft includes an open section through which an outer delivery catheter could be introduced that would provide a means to deliver the, hemostatic members to the aneurysm after the stent graft had been placed. Afterward, another section of the stent graft would be introduced through the original stent graft and positioned over the open section. A second option would be to include a sleeve or other type of valve in the graft material through which the delivery system could be introduced. The valve would then close to prevent leakage of blood. One example of a hemostatic closure member delivery system for treatment of an aneurysm would comprise a series of hemostatic members placed adjacently over a wire guide and loaded into an outer sheath member, such as an introducer sheath or delivery catheter, typically with the assistance of a pusher member. A second method involves loading one or more closure members into a loading cartridge which is inserted into the delivery catheter, whereby a pusher member urges them into the catheter's passageway for final deployment. In one method of deployment, the pusher member individually deploys the hemostatic member or members loaded in the catheter. This procedure is repeated with additional closure members until the aneurysm is filled. Alternatively, the closure member(s) can be expelled from the delivery catheter by infusing saline or another fluid via a syringe through a side port in the delivery system. This method advantageously pre-hydrates the closure member prior to it reaching the deployment site in the body.

In another aspect of the invention, the hemostatic member and delivery system is adapted for delivery into an aneurysm, such as an abdominal aortic aneurysm, such that the delivery catheter is positioned outside of the graft prosthesis, between the graft and the vessel wall. The graft prosthesis is then deployed, leaving the catheter tip inside the excluded aneurysm. This placement method takes advantage of the fact that the technique is already well known for placement of contrast media infusion catheters in this manner. Conveniently, the same catheter for infusion of contrast can be used for the delivery of the hemostatic members. Another advantage is that the graft prosthesis need not be modified to provide temporary access into the aneurysm so that the catheter, which would likely be the case if the hemostatic members are to be delivered from the inside of the graft prosthesis.

In yet another aspect of the invention, the closure member construct comprises a plurality of layers of the second sheet material, such as a single-layer SIS or another biomaterial, preferably lyophilized, that are configured to readily separate in the presence of bodily fluid. The separating layers create a large amount of surface area to absorb fluid and fill a body lumen or cavity when deployed singularly or as a multiplicity of closure members. SIS or other ECM sheet material typically has superior remodeling properties over sponge material, which is subject to additional processing steps, such as cross-linking and comminution that may degrade the matrix structure and growth factors therein and thus, represents a construct that may be more advantageous in clinical situation where rapid swelling is less important than the need to stimulate remodeling by native tissue within a body lumen, such as when attempting the exclusion of an aneurysm.

In a first embodiment, the layered sheet closure member is formed by rolling one of more sheets of SIS to form a tightly rolled configuration that optionally, but not necessarily, includes a functional pathway or lumen extending therethrough. In a second embodiment, the closure member is created from a stack of individual sheets that are either cut into a tubular construct or a squared/rectangular shaped construct that are preferably unattached to one another or partially laminated such that they readily separate when exposed to fluid. In a third embodiment, one or more sheets of material are rolled around a somewhat rigid or semi-rigid core member that in one preferred embodiment, comprises two narrow strips of SIS that are tightly intertwined or braided into an elongate member that is air-dried. The elongate twisted member acts as a mandril that facilitates the rolling of the sheet to form the construct and is absorbed or replaced with adjacent tissue along with the sheet layers following deployment in the body. To facilitate rapid separation of layers of material in each of the above embodiments, a closure member may include one or more longitudinal splits extending the length of the construct. The closure member can be formed by rolling or stacking hydrated ECM sheets, then lyophilizing them, which may result in some degree of lamination between layers of material. Alternatively, the sheet or sheets may be lyophilized first, then rolled or stack to produce a looser construct than may facilitate entry of fluid between the layers of material. A less dense ECM material, such as stomach mucosa, can also represent an alternative larger-cell material that when lyophilized has superior swelling properties similar to sponge material.

In another aspect of the present invention, the closure member is a fallopian tube member which after insertion into a fallopian tube, occludes the tube and blocks sperm from contacting a released egg, thereby preventing conception. In one embodiment, the fallopian tube member includes a loop-shaped metal frame, a first material, a radiopaque binding wire, and a second material, such as a sheet of biomaterial, which adds structural integrity. The first material may include, a sponge-like or foam material, which is capable of absorbing blood and fluid, a lyophilized sheet of SIS, or a sheet of air-dried SIS. The second material may be a sheet of SIS.

The fallopian tube member may be formed around a delivery catheter with an outer wall, a distal end, and a lumen extending therethrough. Two openings are provided opposite each other in the distal end of the delivery catheter transverse to the lumen. The metal wire or frame is threaded through the first opening, the lumen, and exits the second opening. The metal wire is then formed into a loop-shaped frame. Thereafter, a guide wire catheter with a distal end and a lumen extending therethrough is advanced through the delivery catheter until the distal end of the guide wire catheter extends beyond the distal end of the delivery catheter and the loop-shaped metal frame. A first material, which may be sponge-like, is wrapped around the distal end of the guide wire catheter and then a radiopaque binding wire is wrapped around the loop-shaped frame and the first material. In one embodiment, a second sheet of material is then wrapped around the loop-shaped frame, the first material, and the radiopaque binding wire. The ends of the loop-shaped frame are then trimmed flush with the outer wall of the delivery catheter. The frame, as defined herein, may assume a multiplicity of configurations and may comprise more than one component. The primary function of the frame is to have a portion thereof be able to engage the walls of the vessel to anchor the fallopian tube member therein and/or to cause trauma to the walls to encourage migration of fibrocytes into the member material to encourage tissue ingrowth that allows the fallopian tube member to become a permanent occlusion to prevent the passage of gametes (eggs or sperm) or other material.

One method of delivering the fallopian tube member into a fallopian tube includes the steps of providing a uterine introducer catheter which is inserted transcervically through a uterus to the ostium. The delivery catheter and coaxial guide wire catheter with fallopian tube member formed thereon are then advanced through the uterine introducer catheter. Once the fallopian tube member is positioned, the guide wire catheter is withdrawn. As the guide wire catheter is withdrawn, the fallopian tube member is deployed. The delivery catheter and introducer catheter are then removed.

In another aspect, provided is a method for plugging a bodily passageway. The method includes providing an implantable plug member suitable for delivery to the bodily passageway, wherein the passageway is a gastroenteric fistula, the implantable plug member having a first end and a second end and including one or more sheets of a biocompatible extracellular matrix material harvested from collagenous-based mammalian tissue and processed to remove cells with the one or more sheets, prior to implantation, including adjacent layers contacting one another and providing biocompatible extracellular matrix material extending across the full width of the plug member for closing the bodily passageway with the biocompatible extracellular matrix material upon implantation, the extracellular matrix material, prior to implantation, forming an exposed outer surface of the plug member between said first end and said second end of the plug member and being effective upon implantation to stimulate angiogenesis and tissue ingrowth from adjacent native tissue such that the passageway becomes occluded with native tissue of the patient. The method also includes delivering the plug member to the bodily passageway such that the plug member provides the biocompatible extracellular matrix material extending across the bodily passageway so as to close the passageway with the biocompatible extracellular matrix material.

In another aspect, provided is a method for plugging a bodily passageway. The method includes providing a plug member suitable for delivery to the bodily passageway, wherein the passageway is a gastroenteric fistula, the plug member including one or more sheets of a remodelable extracellular matrix material stabilized by compression to provide an implantable construct that, prior to implantation, includes adjacent layers of the one or more sheets contacting one another with the remodelable extracellular matrix material extending across the full width of the implantable construct for closing the bodily passageway with the remodelable extracellular matrix material upon implantation, the remodelable extracellular matrix material obtained in sheet form from a collagenous-based tissue source and effective to become infiltrated and replaced by native tissue upon implantation such that the bodily passageway generally becomes permanently occluded. The method also includes delivering the plug member to the bodily passageway so that the plug member provides the remodelable extracellular matrix material extending across the bodily passageway so as to close the passageway with the remodelable extracellular matrix material.

In another aspect, provided is a method for closing a passageway in a body of a patient. The method includes providing an implantable construct suitable for delivery to the passageway, wherein the passageway is a fistula, the implantable construct including a remodelable extracellular matrix sheet material isolated as a sheet material from a collagenous-based tissue source and being effective upon implantation to stimulate the ingrowth of native tissue into the extracellular matrix sheet material so that the extracellular matrix sheet material becomes infiltrated and replaced by native tissue of the patient in said passageway for closing said passageway, the extracellular matrix sheet material being stabilized in a compressed, rolled configuration in said implantable construct with the remodelable extracellular matrix sheet material extending across the full width of the implantable construct. The method also includes delivering the implantable construct to the passageway such that the implantable construct provides the extracellular matrix sheet material extending across the passageway so as to close the passageway with the extracellular matrix sheet material.

BRIEF DESCRIPTION OF THE DRAWINGS

FIG. 4 depicts a partially sectioned view of the hemostatic delivery subassembly, including the hemostatic member of FIG. 1 prior to being loaded into an introducer sheath.

FIG. 5 depicts a partially sectioned view of the hemostatic member delivery apparatus.

FIGS. 10-12 depict views of embodiments of hemostatic members comprising folded material.

FIG. 13 depicts an embodiment of the hemostatic member comprising only a first material.

FIGS. 14-15 depict an embodiment of the present invention being introduced through a stent graft to treat an aneurysm.

FIG. 16 depicts a partially sectioned view of the delivery of FIGS. 14-15.

FIG. 20 depicts a side view of the apparatus of FIGS. 17-19.

FIGS. 22-29 depict steps in the formation of the fallopian tube member depicted in FIG. 21.

FIGS. 40-41 depict methods of loading the embodiment of FIG. 32 into a loading cartridge.

FIG. 42 depicts the embodiment of FIG. 32 being formed within the loading cartridge using the method of FIG. 41.

DETAILED DESCRIPTION

Figure 1:
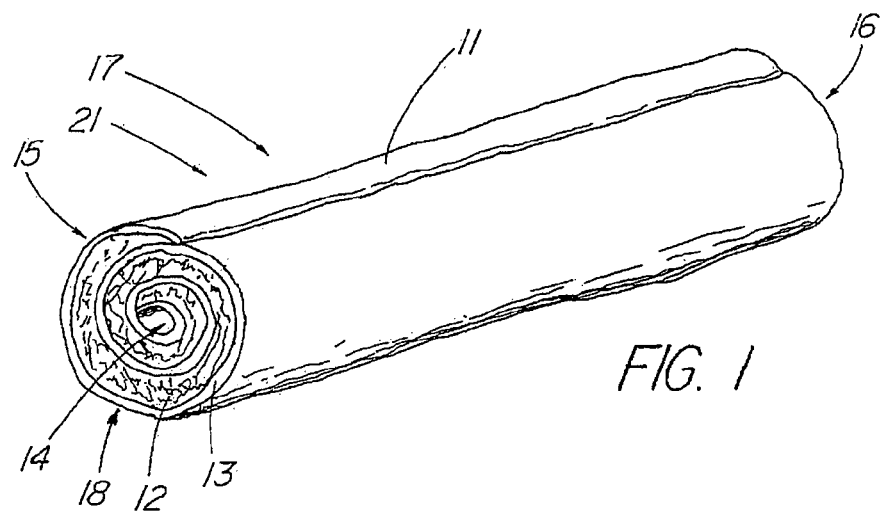
FIG. 1 depicts a pictorial view of an illustrative embodiment of the present invention.

In one embodiment of the present invention, depicted in FIGS. 1-16, the closure member is a hemostatic member 11 which is delivered to a treatment site within the body of a patient to provide an external hemostatic seal or intravascular occlusion to prevent blood flow, such as from a blood vessel 48 punctured during a procedure using an introducer sheath 27 to gain access of a patient's artery or vein, or to fill an aneurysm 58, especially where a stent graft 57 has been placed. The hemostatic member 11 comprises a construct that is able to absorb blood and swell in diameter, yet has sufficient structural integrity in its expanded state to exert a gentle expansile force that provides a more effective seal for achieving hemostasis than collagenous foam alone, particularly in larger puncture channels (above 8 Fr). The illustrative hemostatic member 11, depicted in FIG. 1, includes a rolled configuration 17 comprising a layer 18 of two materials formed by rolling together a first, sponge or foam-like material 12 capable of greatly expanding in diameter as it absorbs blood, and a second, non-sponge material 13 comprising a sheet of a biomaterial, such as small intestinal submucosa (SIS) or another extracellular matrix (ECM). Other possibilities include pericardium, liver basement membrane, or other membranes or sheets harvested or derived from collagenous-based tissue. Possible first materials include lyophilized SIS sponge or other ECM materials, non-extracellular collagen sponge (such as bovine-derived collagen), or synthetic hemostatic materials such as GELFOAM® (Pharmacia Corporation, Peapack, N.J.). In the illustrative embodiment, the first material 12 includes a small square (e.g., 2-3 cm) of SURGISIS™ Soft-Tissue Graft (SIS) (Cook Biotech, Inc., West Lafayette, Ind.) while the second material includes a similar-sized sheet of sponge comprising lyophilized and cross-linked SIS, typically about 1 mm in thickness. Animal studies suggest that the illustrative hemostatic member 11 can be used to effectively seal vessel punctures made by introducer sheaths having an O.D. up to 16 Fr. While naturally derived biomaterials, particularly bioremodelable materials like SIS, are generally preferred, synthetic materials, including those into which growth factors are added to make them bioremodelable, are also within the scope of this invention.

Figure 2:
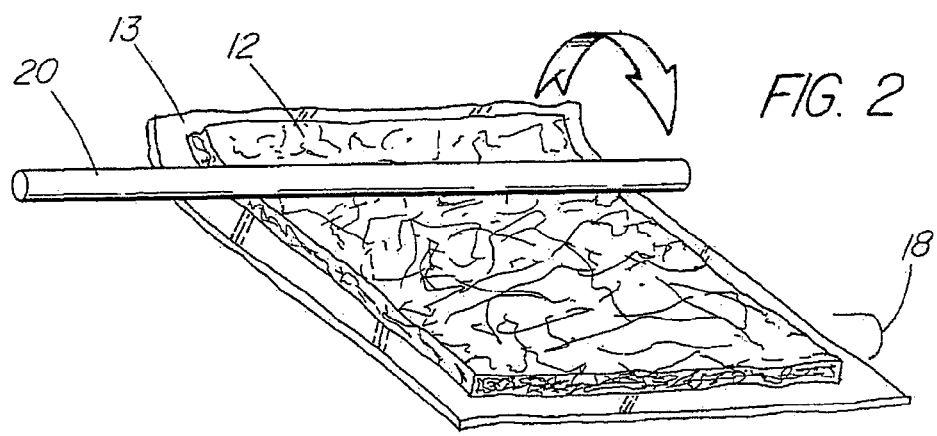
FIGS. 2-3 depict steps in the formation of the hemostatic member of FIG. 1.
Figure 3:
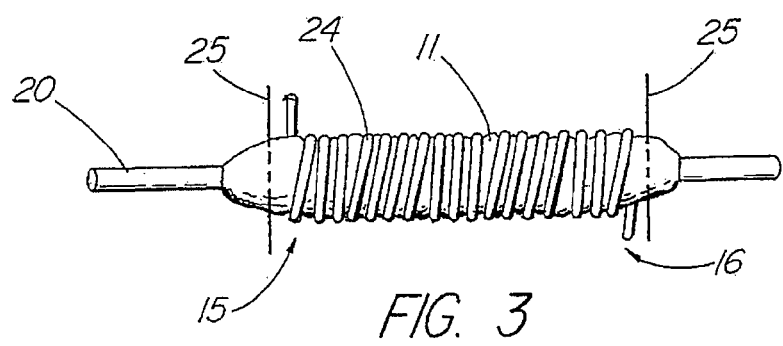

FIG. 2 depicts the formation of the rolled hemostatic member 11 of FIG. 1, whereby the lyophilized SIS sheet 12 is laid upon the non-lyophilized SIS sheet 13, which typically has been pre-wetted. The two materials 12,13 form a single layer 18 which is rolled around a rolling aid 20, such as a section of 0.010" stainless steel wire, to form a construct that assumes a tightly-compressed state 21 in which it will remain until deployment. After the hemostatic member 11 has been rolled into the compressed state 21, a binding or constraining means 24, such as a piece of elastic suture, is wrapped around the hemostatic member for a few minutes or hours until the compression has been stabilized and the construct will remain in that state. The binding means 24, which could also include any wrapping or compressive mechanism, such as a press, is then removed. The rolling aid 20 is also removed, creating a functional passageway 14 within the hemostatic member 11 that allows it to be loaded over a catheter or wire guide as will be discussed later. After removal of the rolling aid 20, the ends of the rolled construct are truncated along a pair of cut lines 25 to create the first and second ends 15, 16 of the hemostatic member. The illustrative hemostatic member 11 is capable of expanding to 6-10× its original volume (typically about twice its diameter) in the presence of blood, the majority of that expansion contributed by expansion of the first, sponge material 12. While the SIS sheet 12 of the first material is capable of swelling as well, e.g., from 100µ to 200µ, its primary function is to provide structural integrity that allows the hemostatic member 11 to radially expand in a controlled manner, such as by unrolling or unfolding, while being able to exert a gentle force or pressure against tissue to provide a useful degree of 'bite' or fixation. In a traditional foam collagen plug, the collagen swells until it contacts adjacent tissue, but the blood-soaked plug at that point, does not have a sufficient constitution to press outward against the walls of the tissue tract in any clinically meaningful way, particularly in larger tissue channels (i.e., above 8 Fr). The SIS sheet 13, which comprises an intact section of tissue that is harvested from porcine intestine, sterilized, and processed to remove the muscular layers and cellular debris, has superior linear strength compared to a sheet of processed collagen, and the added structural integrity provides additional clinical utility over a typical collagen plug or a hemostatic member comprising SIS foam alone. Therefore, the illustrative hemostatic member 11 of FIG. 1 obtains a clinical benefit from the combination of the separate functions of the two materials 12, 13. One skilled in the art should recognize that the highly absorptive sponge or foam material 12 could be augmented in a number of other ways to achieve some degree of the desired performance characteristics, besides the bi-layer sheet configuration, depicted. For example, the second material 13 could include strips or particles of some other biomaterial or suitable synthetic material more durable than foam that while lacking the absorptive capabilities of the sponge 12, would add increased structural integrity during expansion.

FIGS. 4-5 depict an exemplary hemostatic member delivery apparatus 26 configured for placement of the hemostatic member 11 against the outside of a vessel to seal a puncture. The illustrative hemostatic member delivery apparatus 26 includes a hemostatic member delivery subassembly 65, depicted in FIG. 4, and a standard or modified introducer sheath 27 (e.g., a 6 cm COOK CHECK-FLO® Introducer Sheath (Large Valve, Assembly) (Cook Incorporated), shown in FIG. 5 with a portion of the delivery subassembly 65, which can comprise the standard vascular introducer sheath which has already been introduced during the procedure, or a second introducer sheath, sized for use with the delivery subassembly, to replace the original sheath, which would be exchanged over the original wire guide used in the procedure. Referring to FIG. 4, the hemostatic member delivery subassembly 65 includes the hemostatic member 11 which is placed over a delivery catheter 29, such as a standard 3-4 Fr polyethylene or polytetrafluoroethylene catheter. A wire guide 32 is disposed within the passage 36 of the delivery catheter 29 to assist in re-cannulation of the vessel. The illustrative wire guide 32 comprises a distal floppy or atraumatic portion 33, such as a COOK MICROPUNCTURE™ wire guide (Cook Incorporated) followed by a larger diameter portion 34, such as a standard 0.038" wire guide, which can be soldered over the floppy portion 33. Typically, the two portions 33, 34 measure about 2-3 cm in length, with about a third of that being the floppy portion. The remainder of the wire guide 32 comprises a mandril wire 66, such as a 0.014-0.018" stainless steel wire, which is attached to the two coiled portions 33, 34 and extending proximally where it can be manipulated by the operator.

The larger-diameter portion 34 of the wire guide 32 serves to provide a seal of the passage 36 of the delivery catheter 29 when it abuts the catheter's distal end 35, allowing the operator to control whether blood can flow into the passage 36. This can allow the delivery catheter 29 to include positional monitoring capabilities to indicate whether the hemostatic member 11 is in the vessel, or properly positioned outside the vessel. To accomplish this, a side hole 37 is positioned just distal the first end 15 of the hemostatic member 11 which allows blood in the vessel to communicate with the passage 36, which is otherwise sealed by the wire guide 32. It may also be used for the injection of contrast media or dye. If the operator detects blood flowing from a side port catheter 39 (FIG. 5) that communicates with the passage 36 of the delivery catheter 29, then the side hole 37 and probably, at least a portion of the hemostatic member 11 are both still located within the vessel. However, when blood no longer can be observed flowing from the passage 36 to the side port 39, it is an indication that side hole 37 and hemostatic member 11 are outside of the vessel wall where deployment should occur. A second side hole 38 may be positioned along the delivery catheter 29, typically about 5 mm within the hemostatic member 11, to allow blood to flow to the lumen 14 of the hemostatic member 11, which can lead to more rapid expansion following deployment.

Another component of the hemostatic member delivery subassembly is a pusher member 28 which is disposed over the delivery catheter 29 to abut the hemostatic member 11. The function of the pusher member 28 is to provide a counter force sufficient to hold the hemostatic member 11 in position against the vessel during deployment and the initial stages following hemostasis. The illustrative pusher member typically has a diameter of 6-12 Fr, depending on the size of the hemostatic member 11 and the accompanying introducer sheath, and can be made of a variety of polymers, such a polyurethane, polyethylene, etc. that yield good column strength while preferably, having some degree of lateral flexibility.

The illustrative hemostatic member subassembly includes one component, a loading cartridge 40, which is not part of the hemostatic member delivery apparatus 26 in its final, pre-deployment state. The loading cartridge, which in the example of FIG. 4 includes a section of splittable PTFE sheath (such as the PEEL-AWAY® Introducer Sheath (Cook Incorporated), is configured such that it can facilitate the loading process of the hemostatic member 11 into the proximal end 67 of the introducer sheath 27 by providing a hard, protective sheath or conduit that is easier to push through the proximal opening of the introducer sheath 27. The delivery subassembly 65 is inserted into the opening at the proximal end 67 until the cartridge 40 contacts the proximal end, then the cartridge 40 is peeled back (split apart) as the hemostatic member 11 is inserted into the introducer sheath 27, after which it is discarded.

FIG. 5 depicts the hemostatic member delivery apparatus 26 assembled for deployment with the hemostatic member 11 loaded into the introducer member 27. The pusher member 28 includes a proximal hub 30 which engages and locks with the proximal hub 31 of the delivery catheter 29 so that the two components can be introduced together into the introducer sheath 27. An optional deployment guard 42 is positioned between the introducer sheath 27 and hub 30 of the pusher member 28 and sized so that when the delivery subassembly 65 is fully advanced into the introducer sheath 27, the distal end 15 of the hemostatic member 11 is generally aligned with the distal end 50 of the introducer sheath 27, which is the proper pre-deployment position. The illustrative deployment guard 42 is about 2 cm in length, allowing for full exposure of the hemostatic member 11, which typically is about 1.5 cm in length. In the illustrative embodiment, the delivery catheter 29 extends about 3-4 cm beyond the end of the pusher member 28 and about 2 cm beyond the distal end 50 of the introducer sheath 27 after it has been loaded therein. To deploy the hemostatic member 11 so that it is allowed to fully expand with absorbed blood within the tissue channel, the deployment guard 42 is peeled away and removed such that the introducer sheath 27 can be withdrawn relative to the delivery subassembly 65, which is maintained in place by the operator.

Figure 6:
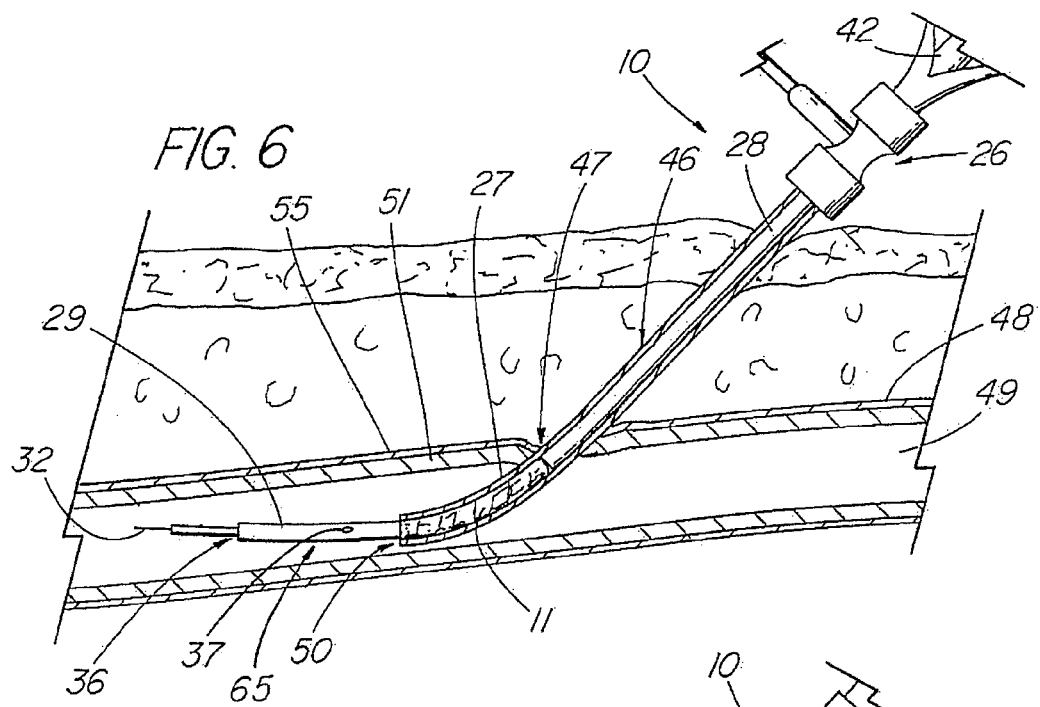
FIGS. 6-7 depict the device being deployed at a vessel puncture site.
Figure 7:
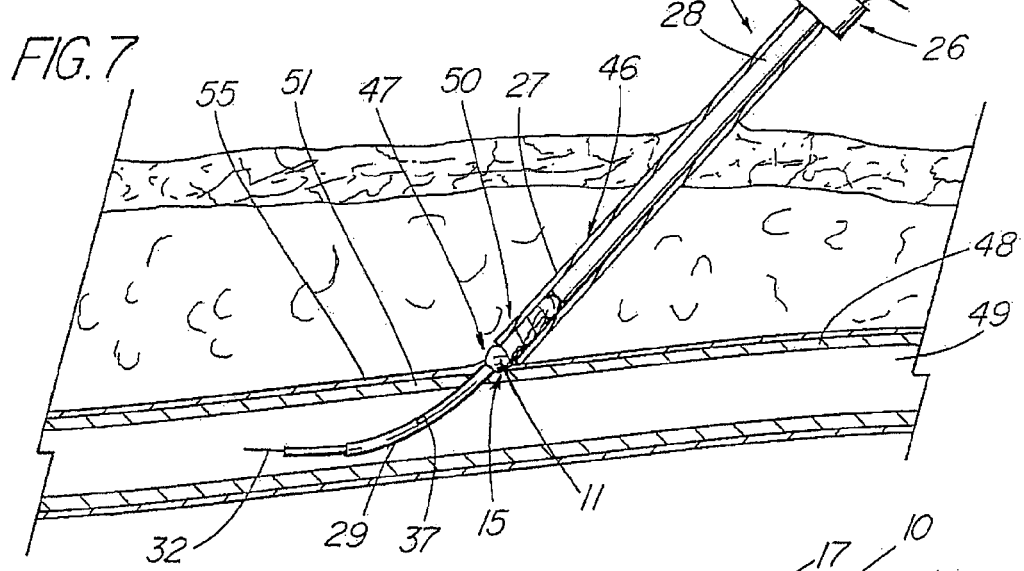
Figure 9:
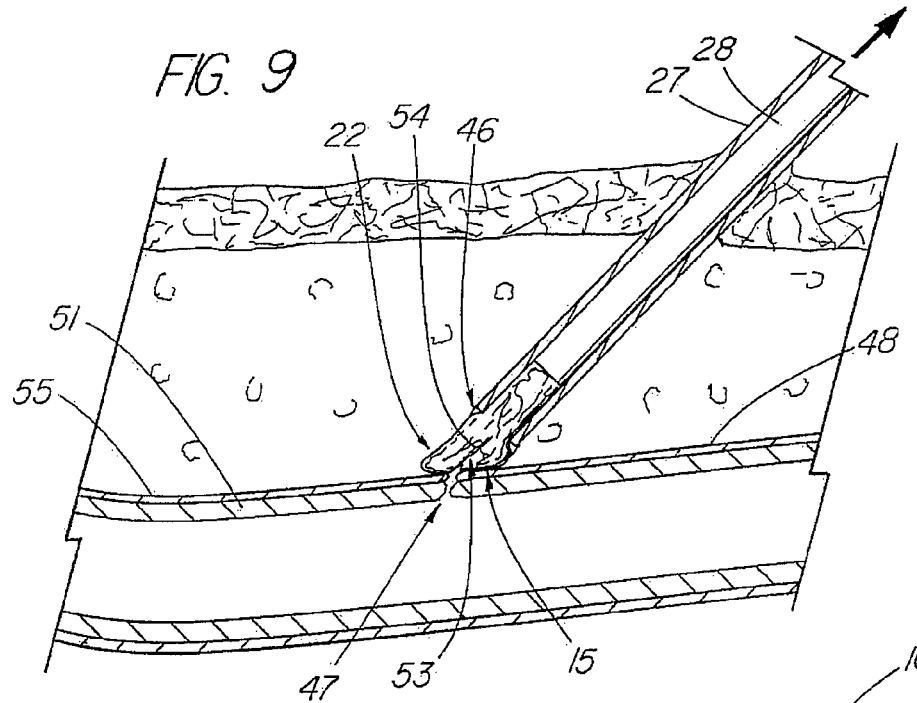
FIGS. 9-9A depict the embodiment of FIG. 8 following deployment.
Figure 9A:
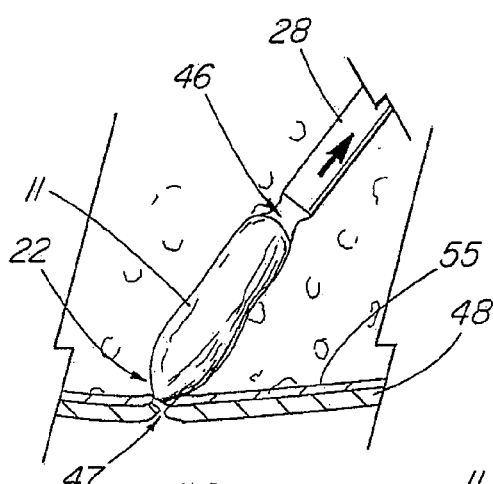

The basic procedure for delivering the hemostatic member 11 against the outside wall of the vessel 48 is shown in FIGS. 6-7. Typically, the procedure to access the vessel will initially involve percutaneous entry of the vessel using a hollow needle, followed by introduction of a wire guide, then a dilator over the wire guide, and ultimately, an intravascular introducer sheath 27, the latter typically to provide a conduit for introducing another medical device, such as a catheter, retrieval device, etc. Once the procedure is completed and the ancillary instrumentation removed, either the original wire guide is removed, leaving the introducer sheath 27 ready to accept the hemostatic delivery subassembly 65, or the original introducer sheath is removed over the wire guide and a new introducer sheath 27, which is packaged as part of the hemostatic member delivery apparatus 26, is exchanged over the existing wire guide. The original wire guide is then removed and the delivery subassembly 65 is introduced through the new introducer sheath 27. In FIG. 6, the distal end 50 of the introducer sheath 27 is situated within the vessel 48 with the delivery subassembly 65 already having been loaded therein such that the delivery catheter 29 and new wire guide 32 extend from the introducer sheath 27 into the vessel lumen 49. Referring also to FIG. 5 now, the hub 30 of the pusher member 28 and the hub 31 of the delivery catheter 29 are locked together at this point (in FIG. 6), and the deployment guard 42 is in place between the introducer sheath 27 and hub 30 (not shown in FIG. 6) to properly align the hemostatic member 11 within the introducer sheath 27 for deployment. The hemostatic member 11, fully inside the introducer sheath 27 at this point, is at least partially within the vessel, and therefore, is partially exposed to blood at its distal end. Additionally, the first side hole 37 is situated within the vessel at this point, indicating to the operator by the presence of blood through the side port 39 (shown in FIG. 5) that the delivery apparatus 26 needs to be withdrawn from the vessel before deployment can occur. The entire hemostatic member delivery apparatus 26 is partially withdrawn until the distal tip 50 is outside the vessel wall 51 and tunica vascularis 55 surrounding the vessel 48 as shown in FIG. 7. The distal portions of the delivery catheter 29 and the wire guide 32 remain in the vessel lumen 49. Because the tissues of the vessel wall 51 and tunica vascularis 55 are somewhat elastic, the puncture hole 47 created in the vessel 48 begins to contract as soon as the blunt-tipped introducer sheath 27 is withdrawn, such that when the introducer sheath 27 is subsequently re-advanced toward the vessel 48, using gently forward pressure, the tip 50 abuts the vessel wall 51 and does not re-enter the vessel lumen 49. This advantageously positions the distal end 15 of the hemostatic member 11 against the vessel wall 49 for deployment. Furthermore, the presence of the delivery catheter 29 and wire guide 32 through the puncture hole 47 helps to center the hemostatic member 11 over the puncture hole 47 during deployment, which involves removing the deployment guard 42 and withdrawing the introducer sheath 27 while maintaining the delivery subassembly 65 in place, thereby fully exposing the hemostatic member 11 to blood exiting the puncture hole 47. At deployment, the wire guide 32 either can be advanced to open the passage 36 of the delivery catheter 29 such that blood can flow to the pathway or lumen 14 of the hemostatic member 11 via the second side hole 37, or both the delivery catheter 29 and wire guide 32 can be withdrawn, thereby hastening the absorption of blood via the hemostatic member lumen 14. In either case, the delivery catheter 29 and wire guide 32 must be removed before full deployment occurs. At deployment, the illustrative hemostatic member 11 unfolds as the foam material rapidly swells with blood, closing the lumen 14 left by the withdrawn delivery catheter 29. As shown in FIGS. 9 and 9A, the hemostatic member quickly assumes the expanded (wet) state 22 and fills the tissue channel 46, thereby sealing the puncture site 47. For the first few minutes after deployment (e.g., 4-5), the pusher member 28 is maintained in position to provide a counter force while the hemostatic member 11 is fully expanding. Afterward, the pusher member 28 is removed from the tissue channel 46, as shown in FIG. 9A, and external pressure or mechanical compression is typically applied over the site until the formation of thrombus results in the stabilization of hemostasis. The time required for external compression varies according to the patient's blood chemistry, anticoagulant treatment, and the size of the puncture hole 47.

Figure 8:
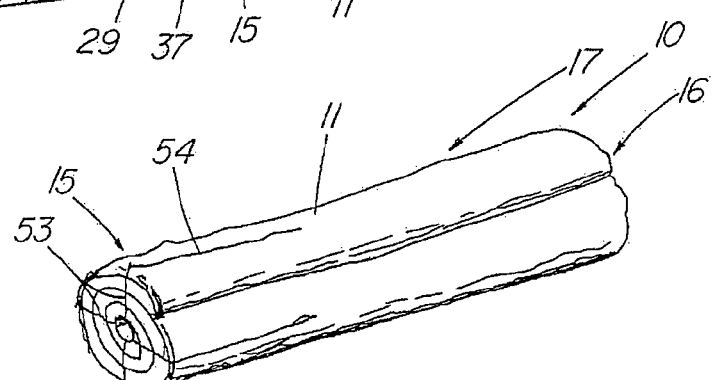
FIG. 8 depicts a pictorial view of a hemostatic member having distal longitudinal slits.

FIGS. 8-9 depict a hemostatic member 11 that includes a modification intended to facilitate more rapid and complete sealing of the area surrounding the puncture site 47. As shown in FIG. 8, the distal 25-30% portion about the first end 15 of the hemostatic member 11 includes a pair of slits 53, extending therethrough and located 90° with respect to one another such that four longitudinal sections 54 or quadrants are formed. It would also within the scope of the invention for the slits 53 to extend only partially through the width hemostatic member 11. In the presence of blood, these sections 54 function to spread laterally outward, as depicted in FIG. 9, to more quickly provide a broad surface contact the outer vessel wall 51 and tunica vascularis 55 and quickly seal the puncture site 47. The remaining, uncut portion toward the second end 16 functions to provide the structural integrity to the hemostatic member 11. During deployment of the embodiment of FIGS. 8-9, the introducer sheath 27 may be withdrawn only to expose the portion having the slits 53, before eventually exposing the entire hemostatic member 11 to blood (FIG. 9A). While the illustrative embodiment includes a pair of slits 53, a single slit 53 or more than two slits 53 may also provide a clinical benefit over a solid, uncut hemostatic member 11. Additionally, the slits 53 can comprise a lesser or greater portion of the length of the hemostatic member 11 compared to the illustrative embodiment.

Figure 10:
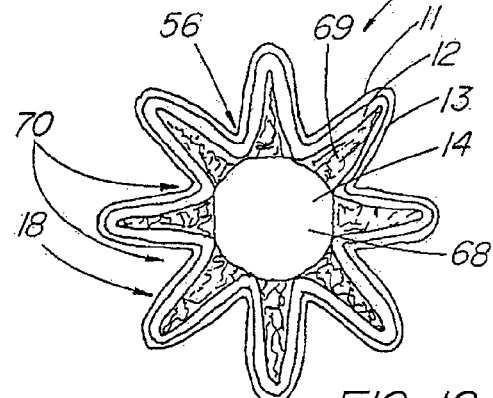
Figure 11:
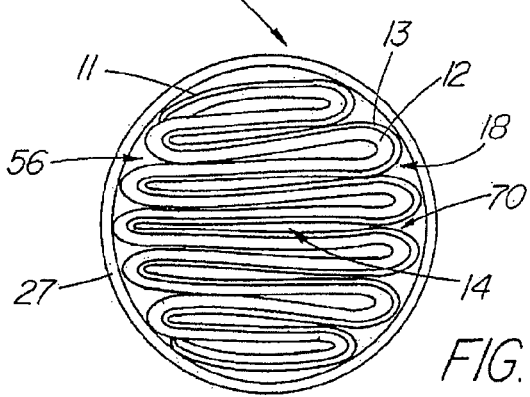

While a hemostatic member 11 comprising the rolled configuration 17 depicted in FIGS. 1 and 8 is well-adapted for rapid and effective radial expansion, there are other numerous configurations of hemostatic members 11 that would be included within the present invention. FIGS. 10-12 depict end views of hemostatic members 11 that comprise a folded configuration 56. Expansion occurs when the hemostatic member 11 swells with blood, forcing the layers 18 to unfold, thereby increasing its volume. The embodiment of FIG. 10 includes a series of folds 70 comprising layers 18 of the two materials 12, 13 arranged in a star-like configuration with the foam material 12 on the outside and the adjacent SIS sheet 13 positioned underneath for structural support. In the illustrative embodiment the functional pathway 14 comprises a third, sealant material 68, such as a gel material having hemostatic properties, such as GELFOAM®. The gel does not interfere with the hemostatic member 11 being loaded over a catheter or wire guide, and can be added beforehand or afterward. Another additive to this particular embodiment is a thrombotic agent 69, such as thrombin, powder, placed between the folded layers 70. When blood contacts the thrombin, it causes the formation of fibrinogen, which further speeds hemostasis. Inclusion of such a thrombotic agent 69 would have utility in virtually any embodiment encompassed by the present invention. FIG. 11 depicts a hemostatic member 11 loaded in an introducer sheath 27 where the hemostatic member 11 comprises a series of parallel folds 70 of the first and second materials 12, 13. A catheter or wire guide (not shown) could be introduced through adjacent layers 18 in the center of the construct to form a functional pathway 14 with the layers 18 then conforming around the device. A third embodiment having a folded configuration 56 is depicted in FIG. 12, whereby the folds 70 are arranged in an overlapping pinwheel configuration. The sponge material 12 is located inside of the sheet material 13 in the illustrative embodiment; however, this arrangement can be reversed as it could in any of the other embodiments. In the illustrative embodiment of FIG. 12, a functional pathway 14 is formed between the inside edges of the folds 70.

The inclusion of a functional pathway 14 that advantageously permits the hemostatic member 11 to be loaded over a delivery device, such as a catheter or wire guide, for delivery into or against the vessel is one aspect of the invention that can provide more precise and efficient delivery. Hemostatic devices, such as the embodiment of FIG. 13 which may lack the other aspects of the invention, could be configured to include a functional pathway 14 for delivery in the manner depicted in FIGS. 6, 7, and 9 or other delivery strategies that involve the hemostatic device being delivered over a catheter and/or wire. It should be noted that although the embodiment of FIG. 13 includes only the first, foam or sponge material 12, a hemostatic member 11 comprising only an SIS sponge 12 it is possible to provide a sponge with added structural integrity, depending on the cross-linking agent used, such that the sponge can be compressed more than it typically could otherwise to have greater expandability and be possibly slower to break apart or liquefy in the presence of blood.

In a second use of the hemostatic member 11 of the present invention, the hemostatic member delivery system 26 invention can be modified to deliver the hemostatic member through or around a stent or stent graft, such as graft to treat an abdominal aortic aneurysm (AAA), particularly to cause hemostasis within the aneurysm to help prevent an endoleak such as around the stent graft, through a collateral vessel and back through the artery, through a hole in the graft material, or because the graft material is too porous. In one embodiment depicted in FIG. 14, the hemostatic members 11 are delivered through a modified bifurcated stent graft 57 that includes open section 61 in the stent frame 60 that lacks the covering material 59 that covers the remainder of the stent. The hemostatic member delivery apparatus 26 includes an outer delivery catheter 64, typically made of a flexible polymer, for navigating through the open section 61 and into the aneurysm 58 where a series of hemostatic members 11 are delivered to fill the space and achieve hemostasis. After the hemostatic members 11 are deployed, the interventional radiologist can introduce a second section of stent graft (not shown) to close the open section 61. A second option of introducing a hemostatic member 11 through a stent graft 57 into an aneurysm is depicted in FIG. 15, wherein the flexible delivery catheter 64 is introduced through a valve 62, such as a sleeve of the graft material 59, which forms the opening 61 in the stent graft 57. Such a valve or sleeve could comprise many possible configurations that temporarily permit access to the aneurysm, but any blood leaking back through the valve 62 when closed, if any, would not be clinically important. One skilled in the art should be able to conceive of additional ways to adapt a stent graft so that it could permit introduction of a hemostatic member into the adjacent aneurysm.

In one embodiment of the hemostatic member delivery apparatus 26, depicted in FIG. 16, for achieving hemostasis or pre-emptive hemostasis in an aneurysm or other large space, the hemostatic members 11 are loaded sequentially over a wire guide 32 that extends through the lumen 45 of the pusher member 28 and through outer delivery catheter 64. The pusher member 28 is advanced to urge the hemostatic members 11 from the outer delivery catheter 64, or it is maintained in position while the outer delivery catheter 64 is withdrawn, thereby deploying the distal-most hemostatic member 11. The delivery apparatus 26 of FIG. 16 is merely exemplary and could easily be modified, especially for intravascular delivery to other sites, such as AV fistulas, vessel malformations, or to occlude a vessel.

Figure 19:
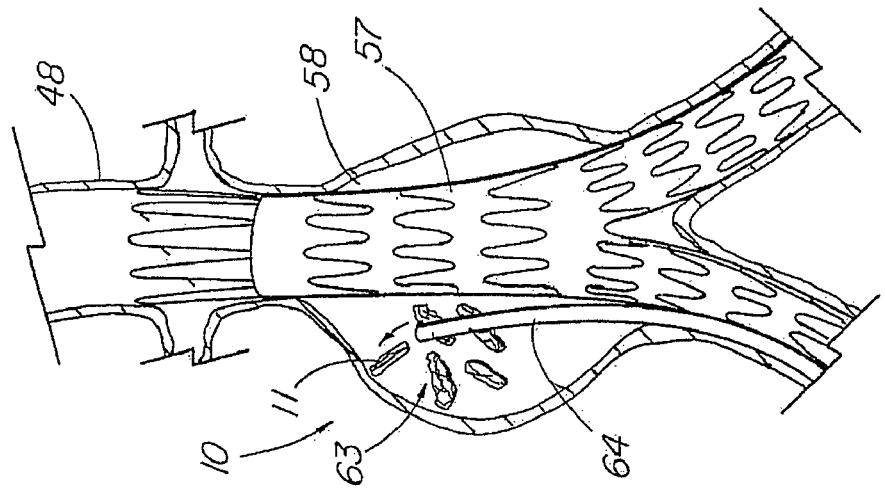
FIGS. 17-19 depict an alternative delivery apparatus and method for filling an aneurysm around a stent-graft prosthesis.
Figure 18:
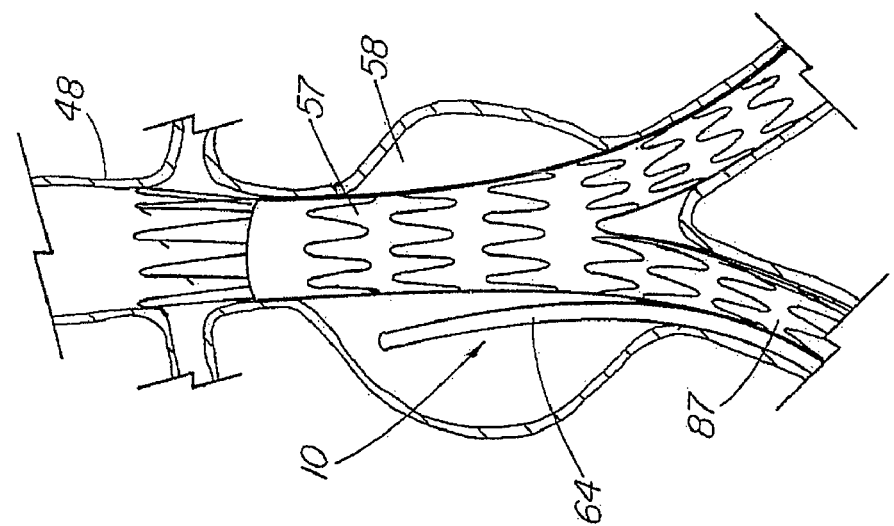
Figure 17:
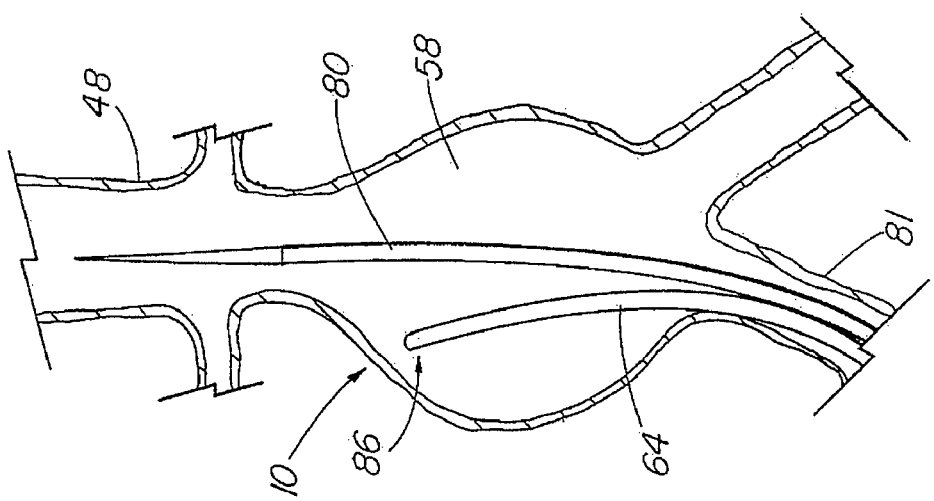

FIGS. 17-19 depict another method and apparatus 10 for delivery a plurality of hemostatic members 63 into an aneurysm 58 in which the delivery catheter or member 64 is situated outside of the graft prosthesis 57 prior to the deployment thereof, obviating the need for requiring access through the graft prosthesis in order to deliver hemostatic members into the aneurysm. In the illustrative method, a catheter, typically one adapted for flushing or infusing the aneurysm with contrast media, is navigated through an iliac artery and placed with the tip 86 is located with the aneurysm to be excluded by a graft prosthesis 57, such as the illustrative ZENITH® AAA Endovascular Graft (FIG. 17). This procedure is typically already part of the overall procedure so that the physician can image the aneurysmal sac under fluoroscopy. In the example procedure depicted, the graft prosthesis delivery catheter 80 is then introduced and graft prosthesis 57 deployed such that the catheter lies outside the stent graft prosthesis 57, such as shown in FIG. 18, where it is positioned between the leg 87 of the prosthesis and the walls of the iliac artery 81 with the tip 86 and distal portion of the catheter 64 still residing within the aneurysm 58. As shown in FIG. 19, a plurality of hemostatic members 63 is then deployed into the aneurysm from the catheter 64 until the desired amount of filling is achieved (usually that required to ensure remodeling of the entire aneursymal sac). Depending on the size of the hemostatic member 11 and aneurysm 58 to be treated, 30 or more hemostatic members 1 may be required to fill the aneurysm sufficiently to prevent endoleaks, particularly of the Type II kind, by blocking or disrupting the inflowing and outflowing collateral vessels which supply the sac with blood. The hemostatic members are deployed by urging them one at a time from the delivery catheter using a well-known means such as a pressurized fluid, (e.g., saline) or a pusher mechanism, such as that shown in FIGS. 15-16.

FIG. 20 depicts an apparatus that uses saline, water, or another fluid to urge the hemostatic member 11 from the delivery catheter 64. The illustrative apparatus includes a delivery catheter, such as a 7-8 Fr FLEXOR® Sheath (Cook Incorporated), with a proximal hub 82 configured to accept a sheath or other device at the proximal end, and further including a side port 84 with an connector 90 for connecting to a infusion supply source 85, such as the illustrative syringe, which is able to infuse a sufficient amount of infusate (generally about 10 cc) to hydrate a single hemostatic member 11, which in the illustrative embodiment, is about 2 cc in volume. In the illustrative embodiment, the hemostatic member 11 is loaded into a cartridge 83 that is sized to be inserted into the proximal hub 82 and passageway 89 of the delivery catheter 64. The cartridge 83 may be sized to accommodate more than one hemostatic member 11. A well-known type of pusher mechanism 28 is used to urge the hemostatic member 11 into the cartridge and then further on into the passageway 89 of the delivery catheter 64, beyond the point where the side port 84 feeds into the catheter 64. The stopcock 91 on the connector 90 is then opened and the infusate is delivered from the syringe 85, thereby urging the hemostatic member through and out of the catheter 64. Additional hemostatic members are loaded and delivered in the same manner until the aneurysm sac is filled.

It may be advantageous to deploy hemostatic members 11 of different sizes when excluding the aneurysm. For example, a shorter hemostatic member 11, e.g., 10-20 mm, may be initially deployed to embolize the collateral vessels, i.e., the lumbar and inferior mesenteric arteries, that can continue to pressurize the sac. Longer hemostatic members, e.g., 25-60 mm, are then deployed into the sac which contribute the majority of the total aneurysm-filling material. Laboratory studies using sheep demonstrated that embolization of the entire aneursymal sac immediately after placement of the graft prosthesis using SIS closure member, advantageously led to a completely organized thrombolitic sac occlusion and elimination of future endoleaks in a significant number of study animals.

FIGS. 32-39 depict a series of closure or hemostatic member 11 embodiments that are particularly well adapted for aneurysm exclusion in that rather than including a sponge material to facilitate rapid and maximum expansion of the construct, the closure member comprises multiple layers of one or more sheets of the second, sheet material 13, such as lyophilized SIS, that are configured to separate upon contact with bodily fluid and swell to help occlude or exclude a body passageway or other space, such as an aneurysmal sac. In the treatment of aneurysms, it is preferred that the material selected is one that advantageously remodels into native tissue, such as connective (e.g., fibrinous) tissue, to permanently exclude the aneurysm, rather than merely being absorbed by the body over time, which could leave the aneurysmal sac still vulnerable to rupture.

Figure 32:
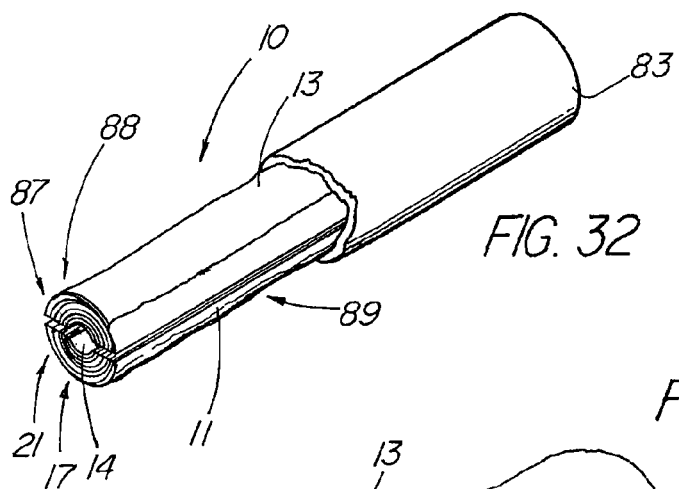
FIGS. 32-33 depict perspective views of an embodiment of the closure member comprising rolled sheet material in a configuration that is split longitudinally, prior to and following deployment.
Figure 33:
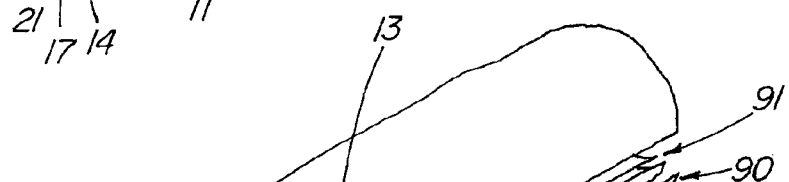

FIG. 32 depicts an embodiment of a closure member 11 comprising a single sheet 12 of a remodelable material, such as SIS or another ECM material, that is formed into a rolled configuration 17. The sheet 11 or closure member 11 is preferably, but not essentially, lyophilized prior to or after being formed into the rolled configuration 17. If the construct is lyophilized after being formed into the rolled configuration 17, hydrated SIS/ECM sheets are used. The closure member 11 is then split longitudinally with the longitudinal split 87 defining a first longitudinal portion 88 and a second longitudinal portion 89 that are held together prior to deployment by an outer constraint, such as a loading cartridge 83 and/or the delivery catheter 64 (FIGS. 17-19). The longitudinal split 87 allows the two longitudinal portions 88, 89 to readily unroll and separate from one another (FIG. 33), thereby creating additional spaces 91 between the layers 90, which results in the bodily fluid quickly coming in contact with additional surface area. Typically, separable layers cause the closure member to swell more rapidly and more fully than it would otherwise. Optionally, the longitudinal portions 88, 89 can be reattached after being split with a weak adhesive, dissolvable threads, or another temporary attachment means that permits separation of the portions in the presence of fluid. A closure member 11 that is split into more than two longitudinal portions is also contemplated. While an intact (unsplit) closure member of a rolled (single sheet) configuration is certainly within the scope of the present invention, the fluid must infiltrate the construct from the outside and the layers are not configured to quickly separate from one another.

One method of loading a split closure member 11 into a cartridge 83, is depicted in FIG. 40. Rather than making the longitudinal split 87 completely through the length of the closure member 11, a short uncut section 98, e.g., 5% of total length, remains at about the second end 15 of the construct. A pulling mechanism 99, such as the illustrative wire or thread, is looped through the longitudinal split 87 and over the uncut section 98 or fed through a hole 101 made therethrough (FIG. 41). In both embodiments, the wire 99 is fed through the passageway 100 at the first end 102 of the loading cartridge 83 and out of the second end 103 thereof so that the closure member can be pulled into the cartridge via the wire or thread. As shown if FIG. 42, the closure member 11 is pulled through until the short uncut section 98 is exposed, along with at least a small portion of the longitudinal split 87. The uncut section 98 is then cut off or otherwise removed such that the (new) second end 15 of the closure member 11 is flush with the second end 103 of the cartridge 83, thereby producing a closure member in which the longitudinal split 87 traverses the entire length of the construct. The split closure member 11 is then pushed into a delivery catheter 64, such as a 8 Fr. FLEXOR® sheath, from which it is deployed into the patient using a technique already described, such at that for the method of deploying the apparatus depicted in FIG. 20.

Figure 34:
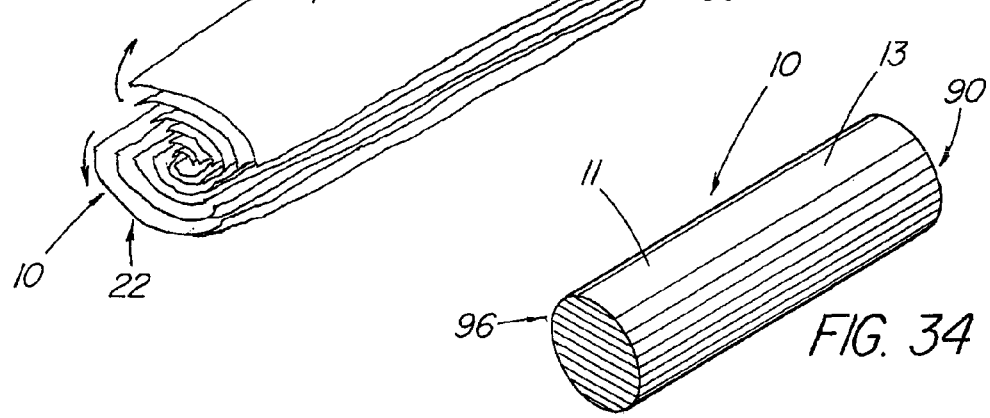
FIGS. 34-36 depict embodiments of a closure member comprising a stack of sheets of material.
Figure 35:
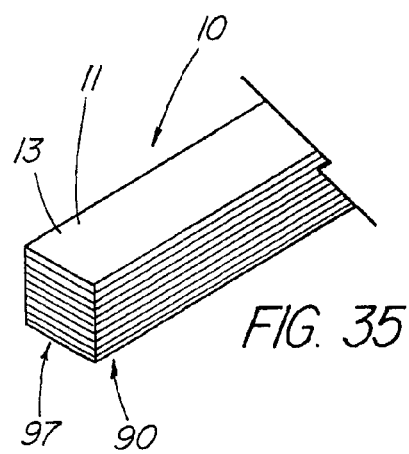
Figure 36:
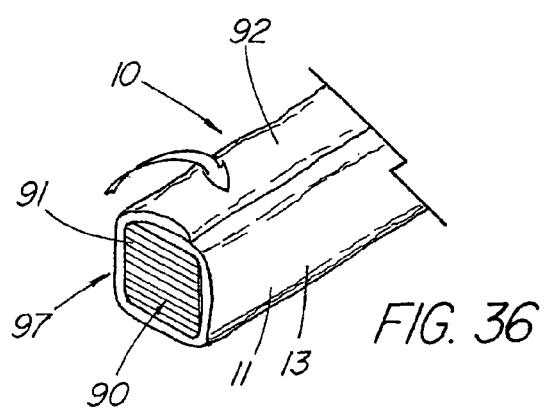

FIGS. 34-36 depicts embodiments of the present invention in which the sheets 12 of SIS or ECM material are stacked to form a multiplicity of layers 90 that are not laminated to one another, thereby permitting separation in the present of bodily fluid following deployment. The embodiment of FIG. 34 comprises a cylindrical or tubular shaped stack 96 of sheets 12 that is formed by either coring a square or irregular stack of sheets, such as shown in FIG. 34, with an appropriate cutting tool or trimming a stack of sheets into a cylindrical shape. The square-shaped stack 97 depicted in FIG. 34 can be loaded into the round passageway of a cartridge or delivery system such that it assumes more of a rounded, generally cylindrical cross-sectional profile, such as shown in FIG. 36. The alternative embodiment of FIG. 36 further includes an outer wrap layer 92 enclosing the multiplicity of layers 90. To facilitate quick separation and migration of fluid into the spaces between the layers 90, the outer wrap layer 92 can remain unattached to itself such that it unrolls more easily to expose the spaces 91 between the layers 90 within, or it can be made such that it readily disintegrates or fractures to fulfill the same purpose. The number of layers 90 (sheets) used to form the illustrative closure member 12 depends on the size of the construct, which is usually determined by the ID of the delivery catheter, the biomaterial used (e.g., stomach submucosa is thicker than SIS) and whether the material is lyophilized before or after it is assembled into the stacked configuration 97. Generally, the closure member 11 used to fill an aneurysm comprises about 20-30 stacked sheets 12, depending on final diameter desired. Alternatively, the layers 90 can be formed by a series of alternating folds of a single sheet (or several sheets), rather than stacking multiple sheets; however, the folds would at least partially block fluid flow into the interlayer spaces and may add additional bulk to the construct, without an accompanying improvement in function.

Figure 37:
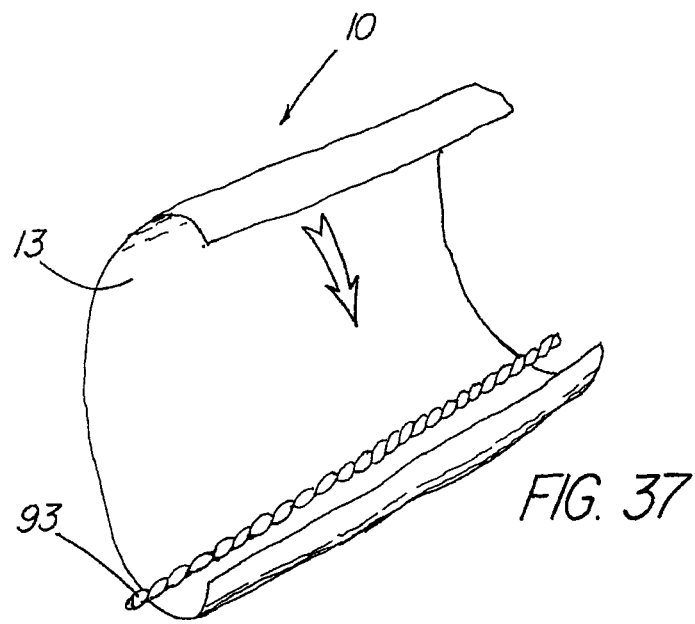
FIG. 37 depicts a view of a closure member being formed by wrapping a sheet of material around a braided core member of same.
Figure 38:
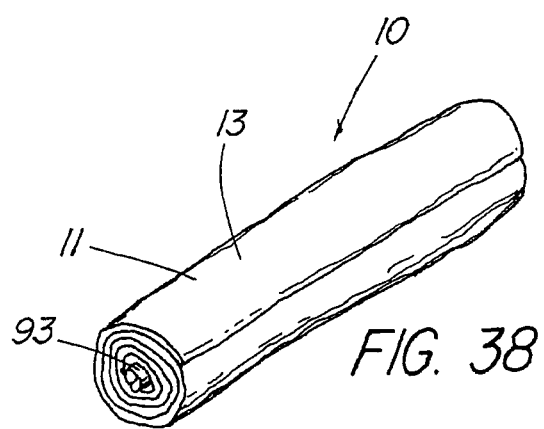
FIG. 38 depicts a perspective view of the formed closure member of FIG. 37.
Figure 39:
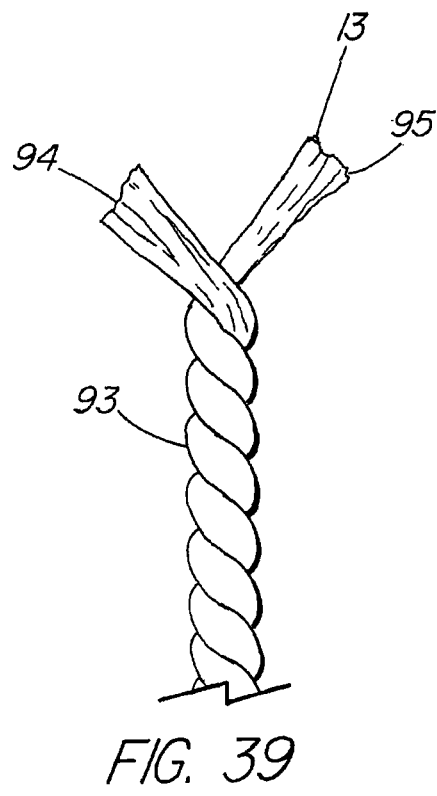
FIG. 39 depicts a top view of the core member of FIG. 37 being formed.

FIGS. 37-38 depict an closure member 11 which further includes a core member 93 at the center of a rolled configuration 17 of a sheet 12 of SIS or other ECM material. As depicted in FIG. 37, the core member 93 acts as a mandril around which the sheet 12 is wrapped to form the construct, thus greatly facilitating the process. Preferably, but not necessarily, the core member comprises a biomaterial that is either absorbed or remodeled by body tissue and which is either the same as or different from that comprising the sheet 12. The illustrative core member 93 comprises a pair of thin, hydrated strips 94, 95 of SIS (e.g., each 2 mm in width) that are intertwined into a single twisted or braided member. To add rigidity that advantageously assists in the rolling process, the core member is air dried after formation. This optional step results in a semi-rigid member 93 that has much less pliability and absorptive ability than the sheet material 12 that surrounds it. If made of SIS or an ECM, the core member 93 may be remodeled into tissue, although it is not essential that it do so, nor is it important that it typically does not contribute significantly to the absorption of blood or other bodily fluid.

Figure 21:
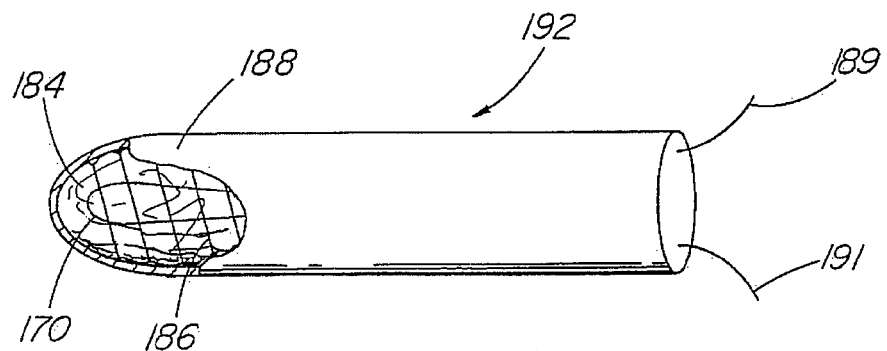
FIG. 21 depicts a partial cross-section of the of the fallopian tube member of the present invention.
Figure 25:
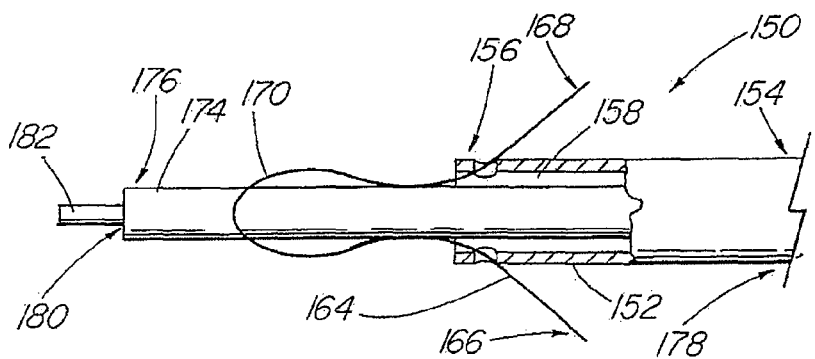

Another embodiment of the closure member 11 of the present invention, depicted in FIGS. 21-31, includes a fallopian tube member which is inserted in the patient's fallopian tube transcervically through the uterus. Tissue in the fallopian tube then grows around the closure member and occludes the fallopian tube. Sperm is blocked from reaching eggs that are released from the ovaries thereby preventing conception. The illustrative fallopian tube member 192 of the present invention as shown in FIG. 21 includes a rolled configuration having a frame 170, such as the illustrative loop-shaped frame ending in barbs 189 and 191, a first layer of material 184, preferably including a biomaterial such as an ECM, a binding wire 186 which also serves as radiopaque marker, and an optional second material 188 comprising a sheet of biomaterial. It should be noted, however, that the fallopian tube member can basically comprise any of the construct embodiments disclosed herein with respect to the configuration of the sheets (rolled vs. folder, stacked, etc.) and the composition of layers (sheet vs. sheet+sponge, etc.).

FIGS. 22-29 depict the formation of the rolled fallopian tube member. A delivery catheter 150 having an outer wall 152, a proximal end 154 end, a distal end 156, and a lumen 158 extending through the length of the catheter is provided. The delivery catheter may range in size, and in a preferred embodiment 5 Fr. Two openings 160 and 162 are formed opposite one another in the distal end 156 of the delivery catheter transverse to the lumen 158. A wire 164 is threaded through opening 160, through the lumen 158 and exits the delivery catheter at opening 162. The wire is sufficiently long that the ends 166 and 168 of the wire extend beyond the outer wall 152 of the delivery catheter 150. The wire 164 may be formed from copper, stainless steel, or other suitable biocompatible metals or metal alloys. The wire 164 may be a round wire having a diameter from about 0.001 to 0.006 inches. In one embodiment, the round wire is about 0.005 inches in diameter. Alternatively, the wire may be a flat wire and have a thickness of about 0.0001 to 0.0005 inches. In one embodiment, the thickness of the flat wire is about 0.0005 inches.

A loop-shaped frame 170 is formed at the distal end of the delivery catheter by pulling the wire 164 through the distal end 156 of the delivery catheter 150 as shown in FIG. 23. Alternatively, the wire may be pre-formed into the loop-shaped frame and each end of the loop threaded through one of the openings in the delivery catheter 150. Another alternative loop-shaped frame 170 is depicted in FIG. 24 wherein the wire 164 crosses over itself to form the loop. A guide wire catheter 174 depicted in FIG. 25 having a distal end 176 and a proximal end 178 is placed in the delivery catheter such that the distal end 176 of the guide wire catheter extends past the distal end 156 of the delivery catheter 150. The guide wire catheter 174 is slidably disposed in the delivery catheter and further has a lumen 180 for accepting a guide wire 182 to aid in the placement of the closure member. Like the delivery catheter, the guide wire catheter also may vary in size, and in one embodiment is a 3 or 4 Fr catheter.

Figure 28:
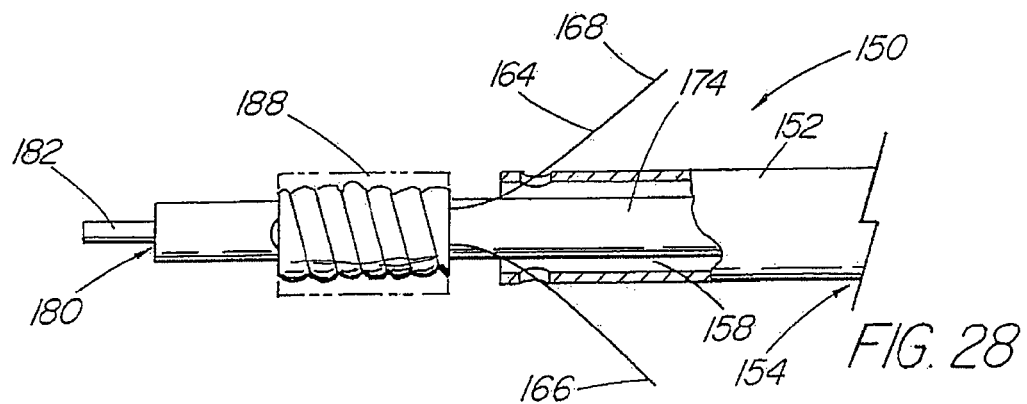
Figure 29:
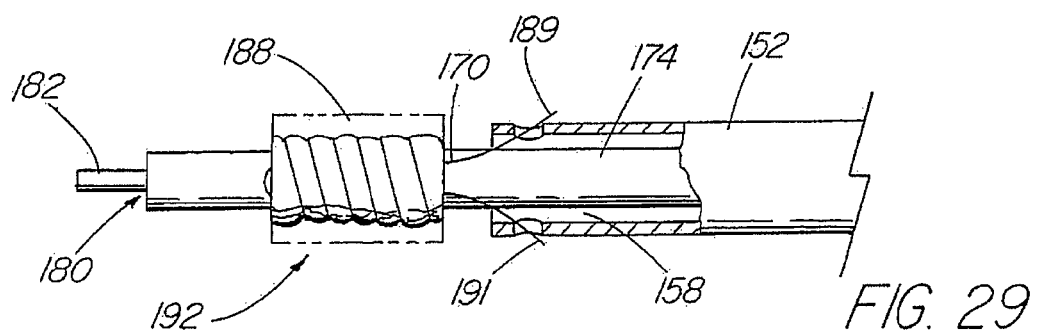
Figure 26:
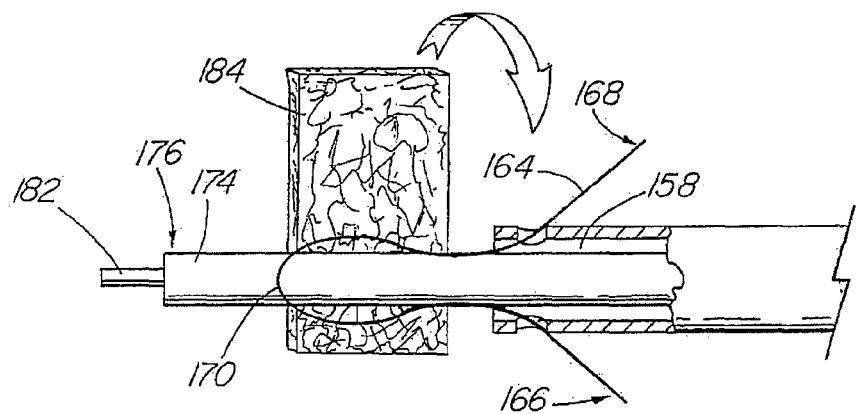
Figure 27:
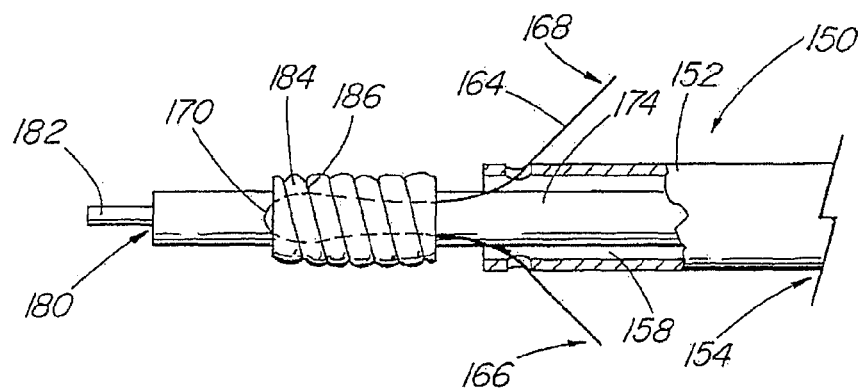

As shown in FIG. 26, a piece of compressed sponge-like material or foam is 184 wrapped around the distal end 176 of the wire guide catheter 174. Alternatively, a single sheet of lyophilized SIS or air dried SIS may be wrapped around the distal end 176 of the guide wire catheter. In another embodiment a tube shaped piece of SIS may be slid over the distal end 176 of the guide wire catheter to cover the end of the catheter. The compressed SIS sponge or tube may or may not be wrapped around the loop-shaped metal frame 170. In one embodiment, the sponge-like material 184 is compressed SIS as previously discussed with respect to the hemostatic member. In the presence of blood or other fluid, the compressed SIS sponge 184 expands about 2-3× its original diameter when inserted into the fallopian tube and occludes a section of the fallopian tube. Subsequently, a wire 186 is wrapped around the sponge-like material 184 and the loop-shaped frame 170 as shown in FIG. 27. The helical wire 186 compresses the sponge and assists in keeping the sponge in place. In addition, the helical wire 186 serves as a marker which can be seen via conventional visualization methods such as x-ray or ultrasound in order to assist in placement of the fallopian tube member. In one embodiment the metal wire 186 is platinum. However, those skilled in the art will realize that other biocompatible metals or metal alloys such as stainless steel, nitinol, etc., may also be used. A thin sheet of material 188 is then wrapped around the loop-shaped frame 170, the sponge-like material 184, and the helical metal wire 186 in order to secure the construct together as shown in FIG. 28. In one embodiment, the sheet of material 188 is SIS which will expand slightly as previously discussed with respect to the hemostatic member and assist in occluding the fallopian tube by encouraging ingrowth of native cells. A binding or constraining means, such as the elastic suture or compressive mechanism shown in FIG. 3 and previously discussed with respect to the hemostatic member, is wrapped around the construct until the compression of the construct has been stabilized and the member remains in the compressed state. The binding means is then removed. The ends 166 and 168 of the loop-shaped frame 170 are then cut off at the outside wall 152 of the delivery catheter 152 to form barbs 189 and 191 (as shown in FIG. 29). The closure member 192 is ready for deployment as shown in FIG. 29. When the member 192 is deployed in a fallopian tube, the truncated ends 189 and 191 of the loop-shaped frame 170 (originally ends 166 and 168) act as barbs and lodge into the wall of the fallopian tube in order to prevent migration of the member 192 in the tube. The trauma caused to the vessel walls also stimulate ingrowth of native cells into the material 184,188, which in the case of ECM materials, allows remodeling or replacement of the ECM with native tissues over time.

While the fallopian tube member 192 may be formed around a guide wire catheter as previously described, it will be appreciated by those of ordinary skill in the art that the fallopian tube member may be formed around a rolling member as described above with respect to the hemostatic member, and then placed over the guide wire catheter prior to insertion of the member.

Figure 30:
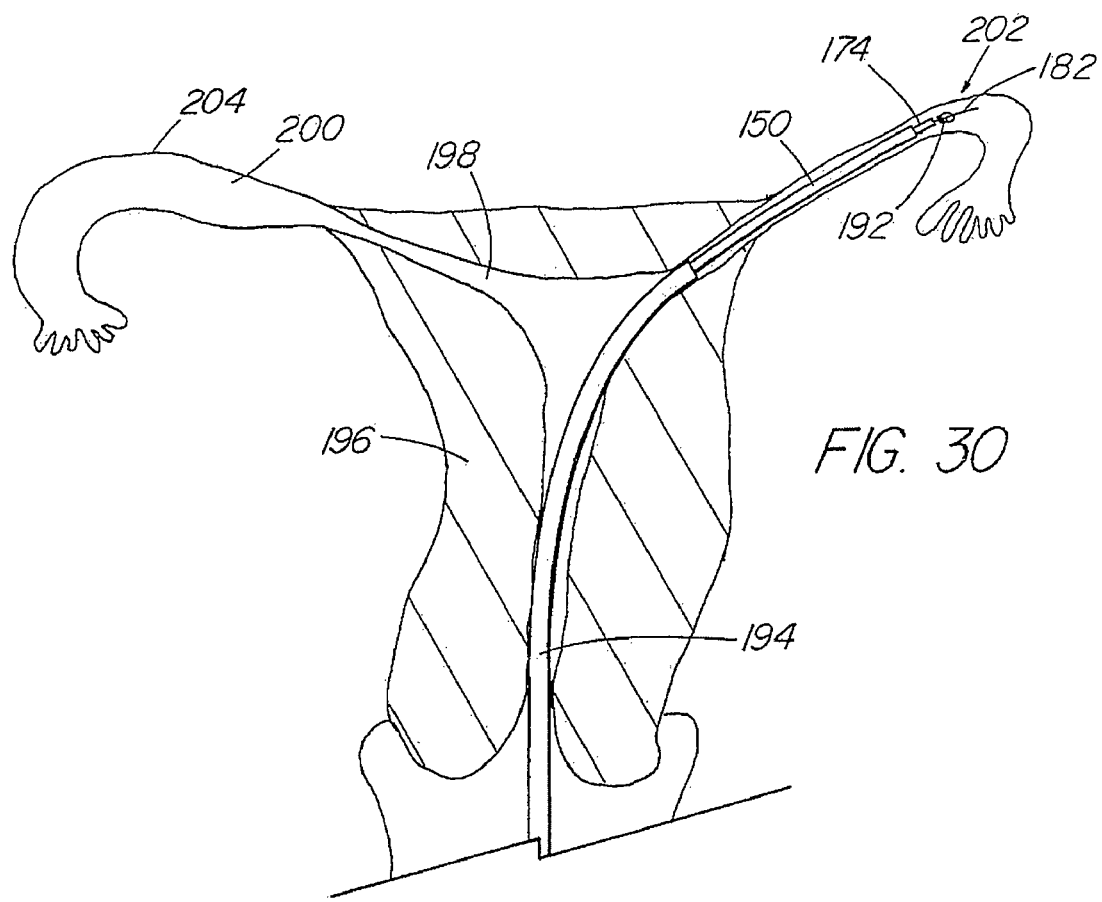
FIGS. 30-31 depict the fallopian tube member shown in FIG. 21 being deployed into a fallopian tube.
Figure 31:
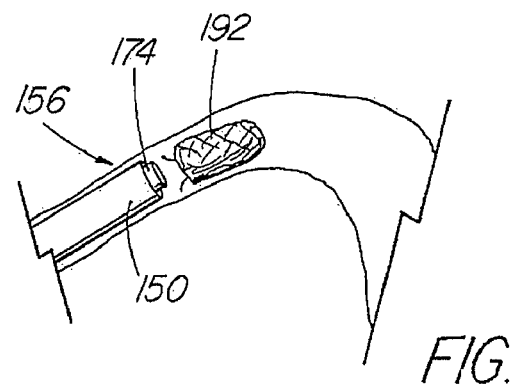

FIGS. 30-31 depict one exemplary delivery apparatus for placement of the fallopian tube member 192 in a fallopian tube in order to seal or occlude the tube. The delivery apparatus in its simplest form is the delivery catheter 150 and the guide wire catheter 174. The basic procedure for delivering the fallopian tube member is shown in FIG. 30. A uterine introducer catheter 194 is inserted transcervically through a uterus 196 to the ostium 198. The delivery catheter 150 with inner coaxial guide wire catheter 174 and fallopian tube member 192 are advanced through the introducer catheter 194 into the fallopian tube 200. The wire marker 186 (not shown) provides good radiopacity and aids in the exact positioning of the fallopian tube member 192 in the tube 200. Once the fallopian tube member is positioned, the guide wire catheter 174 is withdrawn as depicted in FIG. 31. As the guide wire catheter is retracted, a proximal end 202 of the fallopian tube member 192 contacts the distal end 156 of delivery catheter 150 preventing the fallopian tube member from being withdrawn into the delivery catheter. The fallopian tube member 192 has now been deployed over the guide wire and the delivery catheter 150 and introducer catheter are removed 194. On deployment, the sponge-like material 184 and to some extent the sheet material 188 of the fallopian tube member 192 expand thereby occluding the fallopian tube 200. As previously discussed the ends 166 and 168 of the loop-shaped frame 170 of the fallopian tube member 192 lodge in the walls 204 of the fallopian tube and prevent the member 192 from migrating. Thereafter, the sheet of material 188 fuses into the tissue of the fallopian tube 200 and causes the fallopian tube tissue to grow and occlude the tube.

One skilled in the art will realize that the fallopian tube member may be deployed in the fallopian tube by numerous other methods well known in the art. For example, the fallopian tube member 192 may be loaded inside a delivery catheter and deployed in the fallopian tube by pushing the member out of the delivery catheter with the coaxial guide wire catheter. Alternatively, the fallopian tube member may be deployed using fiberoptic scope or hysteroscope.

The advantages of the fallopian tube closure device of the present invention are numerous. Because the fallopian tube member of the present invention may be positioned without surgery, the patient is less likely to suffer substantial blood loss or post-operative infection. Moreover as no incisions are made the patient experiences less pain and recovers from the procedure more quickly than other surgical sterilization procedures. Finally, the fallopian tube members of the present invention can be inserted in a doctor's office under local anesthetic. As a result, the use of the fallopian tube member of the present invention provides a less costly option for sterilization than procedures which require hospitalization.

Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, $27^{th}$ edition.

What is claimed:

1. A method for plugging a bodily passageway, comprising:
    providing an implantable plug member suitable for delivery to the bodily passageway, wherein the passageway is a gastroenteric fistula, the implantable plug member having a first end and a second end and including one or more sheets of a biocompatible extracellular matrix material harvested from collagenous-based mammalian tissue and processed to remove cells with the one or more sheets, prior to implantation, including adjacent layers contacting one another and providing biocompatible extracellular matrix material extending across the full width of the plug member for closing the bodily passageway with the biocompatible extracellular matrix material upon implantation, the extracellular matrix material, prior to implantation, forming an exposed outer surface of the plug member between said first end and said second end of the plug member and being effective upon implantation to stimulate angiogenesis and tissue ingrowth from adjacent native tissue such that the passageway becomes occluded with native tissue of the patient; and
    delivering the plug member to the bodily passageway such that the plug member provides the biocompatible extracellular matrix material extending across the bodily passageway so as to close the passageway with the biocompatible extracellular matrix material.

2. The method of claim 1, wherein the biocompatible extracellular matrix material comprises small intestinal submucosa.

3. The method of claim 1, wherein the one or more sheets are configured to form a generally cylindrical construct.

4. The method of claim 3, wherein the one or more sheets are rolled and compressed to form the construct.

5. The method of claim 3, wherein the one or more sheets are folded and compressed to form the construct.

6. The method of claim 1, wherein the extracellular matrix material includes a lyophilized extracellular matrix material.

7. A method for plugging a bodily passageway, comprising:
    providing a plug member suitable for delivery to the bodily passageway, wherein the passageway is a gastroenteric fistula, the plug member including one or more sheets of a remodelable extracellular matrix material stabilized by compression to provide an implantable construct that, prior to implantation, includes adjacent layers of the one or more sheets contacting one another with the remodelable extracellular matrix material extending across the full width of the implantable construct for closing the bodily passageway with the remodelable extracellular matrix material upon implantation, the remodelable extracellular matrix material obtained in sheet form from a collagenous-based tissue source and effective to become infiltrated and replaced by native tissue upon implantation such that the bodily passageway generally becomes permanently occluded; and
    delivering the plug member to the bodily passageway so that the plug member provides the remodelable extracellular matrix material extending across the bodily passageway so as to close the passageway with the remodelable extracellular matrix material.

8. The method of claim 7, wherein the one or more sheets are configured to form a generally cylindrical construct that includes the remodelable extracellular matrix material spanning the entirety of the length of the generally cylindrical construct.

9. The method of claim 8, wherein the one or more sheets are rolled and compressed to form the construct.

10. The method of claim 8, wherein the one or more sheets are folded and compressed to form the construct.

11. The method of claim 7, wherein the remodelable extracellular matrix material comprises small intestinal submucosa.

12. The method of claim 7, wherein the remodelable extracellular matrix material includes a lyophilized extracellular matrix material.

13. A method for closing a passageway in a body of a patient, comprising:
    providing an implantable construct suitable for delivery to the passageway, wherein the passageway is a fistula, the implantable construct including a remodelable extracellular matrix sheet material isolated as a sheet material from a collagenous-based tissue source and being effective upon implantation to stimulate the ingrowth of native tissue into the extracellular matrix sheet material so that the extracellular matrix sheet material becomes infiltrated and replaced by native tissue of the patient in said passageway for closing said passageway, the extracellular matrix sheet material being stabilized in a compressed, rolled configuration in said implantable construct with the remodelable extracellular matrix sheet material extending across the full width of the implantable construct; and
    delivering the implantable construct to the passageway such that the implantable construct provides the extracellular matrix sheet material extending across the passageway so as to close the passageway with the extracellular matrix sheet material.

14. The method of claim 13, wherein the extracellular matrix material exhibits an angiogenic character.

15. The method of claim 13, wherein the extracellular matrix material includes a lyophilized extracellular matrix material.

16. The method of claim 13, wherein the extracellular matrix material comprises small intestinal submucosa.

17. The method of claim 13, wherein the implantable construct is generally cylindrical.

* * * * *